United States Patent
Lanier et al.

(10) Patent No.: US 7,652,035 B2
(45) Date of Patent: Jan. 26, 2010

(54) CRF RECEPTOR ANTAGONISTS AND METHODS RELATING THERETO

(75) Inventors: Marion Lanier, San Diego, CA (US); Manisha Moorjani, San Diego, CA (US); John Edward Tellew, San Diego, CA (US); John P. Williams, San Diego, CA (US)

(73) Assignees: Neurocrine Bioscience, Inc., San Diego, CA (US); SB Cork, County Cork (IE)

( * ) Notice: Subject to any disclaimer, the term of this patent is extended or adjusted under 35 U.S.C. 154(b) by 243 days.

(21) Appl. No.: 11/576,954

(22) PCT Filed: Oct. 17, 2005

(86) PCT No.: PCT/US2005/037295

§ 371 (c)(1), (2), (4) Date: Apr. 10, 2007

(87) PCT Pub. No.: WO2006/044821

PCT Pub. Date: Apr. 27, 2006

(65) Prior Publication Data

US 2008/0064719 A1     Mar. 13, 2008

Related U.S. Application Data

(60) Provisional application No. 60/620,012, filed on Oct. 19, 2004.

(51) Int. Cl.
| | |
|---|---|
| A61K 31/437 | (2006.01) |
| A61P 25/00 | (2006.01) |
| A61P 29/00 | (2006.01) |
| A61P 37/00 | (2006.01) |
| A61P 9/00 | (2006.01) |
| C07D 471/04 | (2006.01) |

(52) U.S. Cl. .................................. 514/303; 546/119
(58) Field of Classification Search .................. 546/119; 514/303
See application file for complete search history.

(56) References Cited

U.S. PATENT DOCUMENTS

| 7,253,284 B2 * | 8/2007 | DiFabio et al. |
| 7,279,474 B2 * | 10/2007 | Capelli et al. |
| 7,462,622 B2 * | 12/2008 | DiFabio et al. |
| 2007/0004708 A1 * | 1/2007 | Andriotti et al. |
| 2007/0021429 A1 * | 1/2007 | St. Denis |
| 2007/0066640 A1 * | 3/2007 | Castiglioni et al. |
| 2007/0219232 A1 * | 9/2007 | DiFabio et al. |
| 2007/0249625 A1 * | 10/2007 | Busch-Petersen et al. |
| 2007/0287705 A1 * | 12/2007 | Luo et al. |
| 2007/0293511 A1 * | 12/2007 | Luo et al. |

FOREIGN PATENT DOCUMENTS

| GB | 2378702 | * | 2/2003 |
| WO | WO 95/34563 A | | 12/1995 |
| WO | WO98/08847 | * | 3/1998 |
| WO | WO 99/45002 A | | 9/1999 |
| WO | WO01/23389 | * | 4/2001 |
| WO | WO 03/048160 A | | 6/2003 |

OTHER PUBLICATIONS

Pavcovich et al., The Journal of neuroscience : the official journal of the Society for Neuroscience, (Jan. 1, 1997) vol. 17, No. 1, pp. 401-408.*

* cited by examiner

*Primary Examiner*—D. Margaret Seaman
*Assistant Examiner*—Niloofar Rahmani
(74) *Attorney, Agent, or Firm*—Laura K. Madden; Theodore R. Furman

(57) ABSTRACT

CRF receptor antagonists are disclosed which may have utility in the treatment of a variety of disorders, including the treatment of disorders manifesting hypersecretion of CRF in mammals, such as stroke. The CRF receptor antagonists of this invention have the following structure:

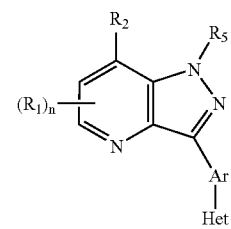

and pharmaceutically acceptable salts, esters, solvates, stereoisomers and prodrugs thereof, wherein $R_1$, $R_2$, n, $R_5$, Ar, and Het are as defined herein. Compositions containing a CRF receptor antagonists in combination with a pharmaceutically acceptable carrier are also disclosed, as well as methods for use of the same.

35 Claims, No Drawings

CRF RECEPTOR ANTAGONISTS AND METHODS RELATING THERETO

This application is a 371 of International Application No. PCT/US2005/037295, filed 17 Oct. 2005, which claims priority of U.S. Provisional Application No. 60/620,012, filed 19 Oct. 2004.

CROSS REFERENCE TO RELATED APPLICATION

This application claims the benefit of U.S. Provisional Application No. 60/620,012 filed Oct. 19, 2004, which is hereby incorporated by reference in its entirety.

TECHNICAL FIELD

This invention relates generally to CRF receptor antagonists, and to methods of treating disorders by administration of such antagonists to a mammal in need thereof.

BACKGROUND OF THE INVENTION

The first corticotropin-releasing factor (CRF) was isolated from ovine hypothalami and identified as a 41-amino acid peptide (Vale et al., *Science* 213:1394-1397, 1981). Subsequently, sequences of human and rat CRF were isolated and determined to be identical but different from ovine CRF in 7 of the 41 amino acid residues (Rivier et al., *Proc. Natl. Acad. Sci. USA* 80:4851, 1983; Shibahara et al., *EMBO J.* 2:775, 1983).

CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., *Science* 213:1394-1397, 1981). Briefly, CRF is believed to initiate its biological effects by binding to a plasma membrane receptor which has been found to be distributed throughout the brain (DeSouza et al., *Science* 224: 1449-1451, 1984), pituitary (DeSouza et al., *Methods Enzymol.* 124:560, 1986; Wynn et al., *Biochem. Biophys. Res. Comm.* 110:602-608, 1983), adrenals (Udelsman et al., *Nature* 319:147-150, 1986) and spleen (Webster, E. L., and E. B. DeSouza, *Endocrinology* 122:609-617, 1988). The CRF receptor is coupled to a GTP-binding protein (Perrin et al., *Endocrinology* 118:1171-1179, 1986) which mediates CRF-stimulated increase in intracellular production of cAMP (Bilezikjian, L. M., and W. W. Vale, *Endocrinology* 113:657-662, 1983). The receptor for CRF has now been cloned from rat (Perrin et al., *Endo* 133(6):3058-3061, 1993), and human brain (Chen et al., *PNAS* 90(19):8967-8971, 1993; Vita et al., *FEBS* 335(1):1-5, 1993). This receptor is a 415 amino acid protein comprising seven membrane spanning domains. A comparison of identity between rat and human sequences shows a high degree of homology (97%) at the amino acid level.

In addition to its role in stimulating the production of ACTH and POMC, CRF is also believed to coordinate many of the endocrine, autonomic, and behavioral responses to stress, and may be involved in the pathophysiology of affective disorders. Moreover, CRF is believed to be a key intermediary in communication between the immune, central nervous, endocrine and cardiovascular systems (Crofford et al., *J. Clin. Invest.* 90:2555-2564, 1992; Sapolsky et al., *Science* 238:522-524, 1987; Tilders et al., *Regul. Peptides* 5:77-84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., *Nature* 297:331, 1982), persistent activation of the electroencephalogram (Ehlers et al., *Brain Res.* 278:332, 1983), stimulation of the sympathoadrenomedullary pathway (Brown et al., *Endocrinology* 110:928, 1982), an increase of heart rate and blood pressure (Fisher et al., *Endocrinology* 110:2222, 1982), an increase in oxygen consumption (Brown et al., *Life Sciences* 30:207, 1982), alteration of gastrointestinal activity (Williams et al., *Am. J. Physiol.* 253:G582, 1987), suppression of food consumption (Levine et al., *Neuropharmacology* 22:337, 1983), modification of sexual behavior (Sirinathsinghji et al., *Nature* 305:232, 1983), and immune function compromise (Irwin et al., *Am. J. Physiol.* 255:R744, 1988). Furthermore, clinical data suggests that CRF may be hypersecreted in the brain in depression, anxiety-related disorders, and anorexia nervosa. (DeSouza, *Ann. Reports in Med. Chem.* 25:215-223, 1990). Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., *Science* 224:889, 1984). While these peptides established that CRF receptor antagonists can attenuate the pharmacological responses to CRF, peptide CRF receptor antagonists suffer from the usual drawbacks of peptide therapeutics including lack of stability and limited oral activity.

Published applications WO 98/43962, which discloses fused or spiro 6,5-bicyclic acid ammonio alkyl ester compounds as prodrugs for integrin receptor antagonists, and WO 97/23480, which discloses heterocyclyl-substituted indazole derivatives as vitronectin receptor antagonists, disclose compounds having a pyrazolo[4,3-b]pyridine core.

Due to the physiological significance of CRF, the development of biologically-active small molecules having significant CRF receptor binding activity and which are capable of antagonizing the CRF receptor remains a desirable goal. Such CRF receptor antagonists may be useful in the treatment of endocrine, psychiatric and neurological conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

SUMMARY OF THE INVENTION

This invention is generally directed to CRF receptor antagonists, and more specifically to CRF receptor antagonists having the following general structure (I):

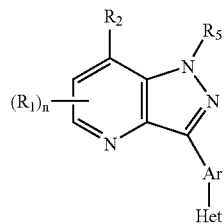

and pharmaceutically acceptable salts, esters, solvates, stereoisomers and prodrug thereof,
wherein:
$R_1$ at each occurrence is independently $C_1$-$C_6$ alkyl;
n is 0, 1 or 2;
$R_2$ is $C_1$-$C_{10}$ alkyl, substituted $C_1$-$C_{10}$ alkyl, aryl, substituted aryl, arylalkyl, substituted arylalkyl, heterocyclyl, substituted heterocyclyl, —$OR_3$, or —$NR_{4a}R_{4b}$;
$R_3$ is $C_1$-$C_{10}$ alkyl, substituted $C_1$-$C_{10}$ alkyl, arylalkyl, substituted arylalkyl, $C_1$-$C_{10}$ alkoxyalkyl, substituted $C_1$-$C_{10}$ alkoxyalkyl, heterocyclealkyl, or substituted heterocyclealkyl;
$R_{4a}$ and $R_{4b}$ are the same or different and independently hydrogen, $C_1$-$C_{10}$ alkyl, substituted $C_1$-$C_{10}$ alkyl, arylalkyl, substituted arylalkyl, heteroarylalkyl, substituted heteroarylalkyl, $C_1$-$C_{10}$ alkoxyalkyl or substituted $C_1$-$C_{10}$ alkoxyalkyl, with the proviso that $R_{4a}$ and $R_{4b}$ cannot both be hydrogen;
$R_5$ is hydrogen or $C_1$-$C_6$ alkyl;
Ar is substituted phenyl, pyridyl or substituted pyridyl; and
Het is heterocyclyl or substituted heterocyclyl.

These and other aspects of the invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

The present invention is directed generally to compounds useful as corticotropin-releasing factor (CRF) receptor antagonists. In a first embodiment, the CRF receptor antagonists of this invention have the following structure (I):

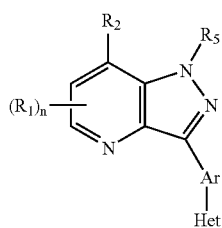

(I)

and pharmaceutically acceptable salts, esters, solvates, stereoisomers and prodrugs thereof,
wherein:
$R_1$ at each occurrence is independently $C_1$-$C_6$ alkyl;
n is 0, 1 or 2;
$R_2$ is $C_1$-$C_{10}$ alkyl, substituted $C_1$-$C_{10}$ alkyl, aryl, substituted aryl, arylalkyl, substituted arylalkyl, heterocyclyl, substituted heterocyclyl, —$OR_3$, or —$NR_{4a}R_{4b}$;
$R_3$ is $C_1$-$C_{10}$ alkyl, substituted $C_1$-$C_{10}$ alkyl, arylalkyl, substituted arylalkyl, $C_1$-$C_{10}$ alkoxyalkyl, substituted $C_1$-$C_{10}$ alkoxyalkyl, heterocyclealkyl, or substituted heterocyclealkyl;
$R_{4a}$ and $R_{4b}$ are the same or different and independently hydrogen, $C_1$-$C_{10}$ alkyl, substituted $C_1$-$C_{10}$ alkyl, arylalkyl, substituted arylalkyl, heteroarylalkyl, substituted heteroarylalkyl, $C_1$-$C_{10}$ alkoxyalkyl or substituted $C_1$-$C_{10}$ alkoxyalkyl, with the proviso that $R_{4a}$ and $R_{4b}$ cannot both be hydrogen;
$R_5$ is hydrogen or $C_1$-$C_6$ alkyl;
Ar is substituted phenyl, pyridyl or substituted pyridyl; and
Het is heterocyclyl or substituted heterocyclyl.

The CRF receptor antagonists of this invention may have utility over a wide range of therapeutic applications, and may be used to treat a variety of disorders or illnesses, including stress-related disorders. Such methods include administering an effective amount of a CRF receptor antagonist of this invention, preferably in the form of a pharmaceutical composition, to an animal in need thereof. Accordingly, in another embodiment, pharmaceutical compositions are disclosed containing one or more CRF receptor antagonists of this invention in combination with a pharmaceutically acceptable carrier and/or diluent.

As used herein, the above terms have the following meaning:

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. Thus, the term "lower alkyl" is interchangeable with the term "$C_1$-$C_6$ alkyl." Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —$CH_2$-cyclopropyl, —$CH_2$-cyclobutyl, —$CH_2$-cyclopentyl, —$CH_2$-cyclohexyl, and the like; while unsaturated cyclic alkyls include cyclopentenyl and cyclohexenyl, and the like. Cyclic alkyls, also referred to as "homocyclic rings," include di- and poly-homocyclic rings such as decalin and adamantyl. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Aryl" means an aromatic carbocyclic moiety such as phenyl or naphthyl.

"Arylalkyl" means an alkyl having at least one alkyl hydrogen atom replaced with an aryl moiety, such as benzyl (i.e., —$CH_2$-phenyl), —$CH_2$-(1- or 2-naphthyl), —$(CH_2)_2$phenyl, —$(CH_2)_3$phenyl, —$CH(phenyl)_2$, and the like.

"Heteroaryl" means an aromatic heterocycle ring of 5- to 10-members and having at least one heteroatom selected from nitrogen, oxygen and sulfur, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, quinazolinyl and oxadiazolyl.

"Heteroarylalkyl" means an alkyl having at least one alkyl hydrogen atom replaced with a heteroaryl moiety, such as —CH$_2$-pyridinyl, —CH$_2$-pyrimidinyl, and the like.

"Heterocycle" (also referred to herein as a "heterocycle ring" or "heterocyclyl") means a 5- to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocycle rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, piperizinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$-morpholinyl, —CH$_2$-pyridyl, —CH$_2$-pyrimidinyl, and the like.

The term "substituted" as used herein means that at least one hydrogen atom on any of the above groups (i.e., alkyl, alkoxy, alkoxyalkyl, aryl, arylalkyl, heteroaryl, heteroarylalkyl, heterocycle or heterocyclealkyl) is replaced with a substituent. In the case of a keto substituent ("—C(=O)—") two hydrogen atoms are replaced. "Substituents" within the context of this invention include halogen, hydroxy, cyano, nitro, amino, alkylamino, dialkylamino, alkyl, substituted alkyl, alkoxy, thioalkyl, haloalkyl, hydroxyalkyl, alkoxyalkyl, haloalkoxy, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)R$_b$, —NR$_a$C(=O)NR$_a$R$_b$, —NR$_a$C(=O)OR$_b$, —NR$_a$SO$_2$R$_b$, —OR$_a$, —C(=O)R$_a$, —C(=O)OR$_a$, —C(=O)NR$_a$R$_b$, —OC(=O)NR$_a$R$_b$, —SH, —SR$_a$, —S(=O)R$_a$, —S(=O)$_2$R$_a$, —OS(=O)$_2$R$_a$, —S(=O)$_2$OR$_a$, wherein R$_a$ and R$_b$ are the same or different and independently hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl.

"Halogen" means fluoro, chloro, bromo or iodo.

"Haloalkyl" means an alkyl having at least one hydrogen atom replaced with halogen, such as trifluoromethyl and the like. Haloalkyl is a specific embodiment of substituted alkyl, wherein alkyl is substituted with one or more halogen atoms.

"Alkoxy" means an alkyl moiety attached through an oxygen bridge (i.e., —O-alkyl) such as —O-methyl, —O-ethyl, and the like.

"Haloalkoxy" means an alkoxy having at least one hydrogen atom replaced with halogen, such as trifluoromethoxy and the like.

"Alkoxyalkyl" means an alkyl having at least one hydrogen atom replaced with alkoxy, such as methoxymethyl and the like.

"Thioalkyl" means an alkyl moiety attached through a sulfur bridge (i.e., —S-alkyl) such as —S-methyl, —S-ethyl, and the like.

"Alkylamino" and "dialkylamino" mean one or two alkyl moieties attached through a nitrogen bridge (i.e., —NHalkyl or —N(alkyl)(alkyl)) such as methylamino, ethylamino, dimethylamino, diethylamino, and the like.

"Hydroxyalkyl" means an alkyl substituted with at least one hydroxyl group.

Embodiments of the invention presented herein are for purposes of example and not for purposes of limitation. In one embodiment of the present invention, (R$_1$)$_n$— represents an alkyl substituent R$_1$ taken n times, where n is 0, 1 or 2. Thus, representative compounds of this invention include the following structures (IIa) through (IId):

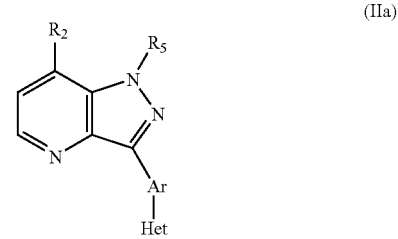
(IIa)

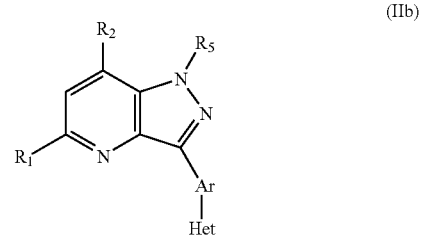
(IIb)

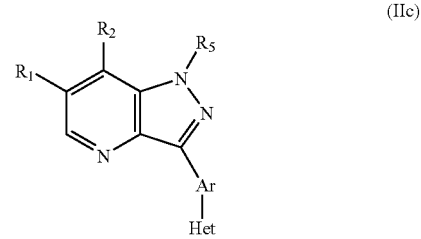
(IIc)

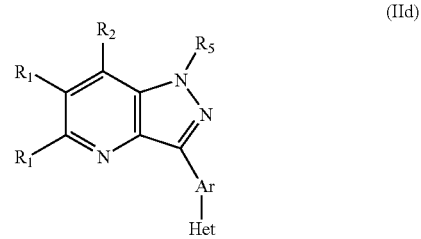
(IId)

In certain embodiments of the invention R$_1$ is C$_1$-C$_6$ alkyl, which may be exemplified by, for example, methyl, ethyl, propyl, isopropyl, butyl and isobutyl.

In further embodiments of the invention R$_2$ is C$_1$-C$_{10}$ alkyl, substituted C$_1$-C$_{10}$ alkyl, aryl, substituted aryl, heteroaryl, or substituted heteroaryl. In certain embodiments R$_2$ is C$_1$-C$_6$ alkyl such as, for example, methyl.

In further embodiments of the invention R$_2$ is —OR$_3$ in the following structure (III) wherein R$_3$ is C$_1$-C$_{10}$ alkyl, substituted C$_1$-C$_{10}$ alkyl, arylalkyl, substituted arylalkyl, C$_1$-C$_{10}$ alkoxyalkyl, substituted C$_1$-C$_{10}$ alkoxyalkyl, heterocyclealkyl or substituted heterocyclealkyl:

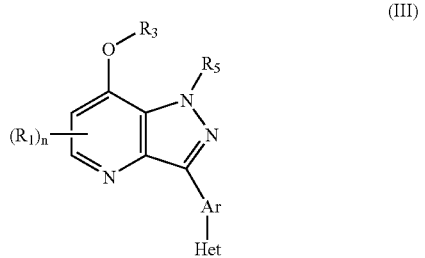

(III)

In further embodiments of the invention where $R_2$ is —$OR_3$, $R_3$ is $C_1$-$C_6$ alkyl, substituted $C_1$-$C_6$ alkyl, $C_1$-$C_6$ alkoxyalkyl or heteroarylalkyl.

In further embodiments of the invention $R_2$ is $C_1$-$C_6$ alkyl or $C_1$-$C_6$ substituted alkyl.

In further embodiments of the invention $R_2$ is —$NR_{4a}R_{4b}$ in the following structure (IV) wherein $R_{4a}$ and $R_{4b}$ are the same or different and independently hydrogen, $C_1$-$C_{10}$ alkyl, substituted $C_1$-$C_{10}$ alkyl, arylalkyl, substituted arylalkyl, heteroarylalkyl, substituted heteroarylalkyl, $C_1$-$C_{10}$ alkoxyalkyl or substituted $C_1$-$C_{10}$ alkoxyalkyl, provided that $R_{4a}$ and $R_{4b}$ cannot both be hydrogen:

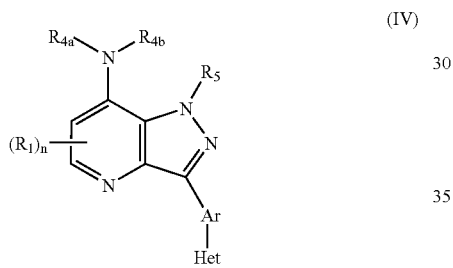

(IV)

In further embodiments of the invention $R_{4a}$ and $R_{4b}$ are independently $C_1$-$C_6$ alkyl. In further embodiments of the invention $R_5$ is hydrogen or $C_1$-$C_6$ alkyl. In further embodiments $R_5$ is methyl.

In further embodiments of the invention Ar is phenyl as shown in the following structure (V) wherein m is an integer 1-4 inclusive and each $R_6$ is independently $C_1$-$C_6$ alkyl, substituted $C_1$-$C_6$ alkyl, $C_1$-$C_6$ alkoxy or halogen:

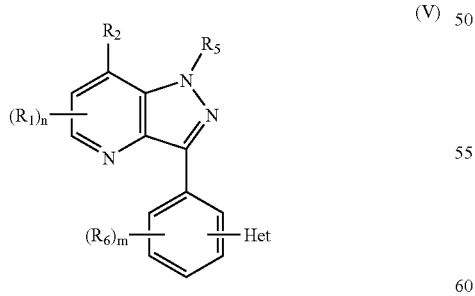

(V)

In certain embodiments each $R_6$ is independently methyl, methoxy or trihalomethyl.

In further embodiments of the invention Ar is pyridyl, which group is bonded to the pyrazolopyridine core through carbon atom numbers 2, 3 or 4 of the pyridyl ring, as shown in the following structures (VIa, VIb and VIc), respectively:

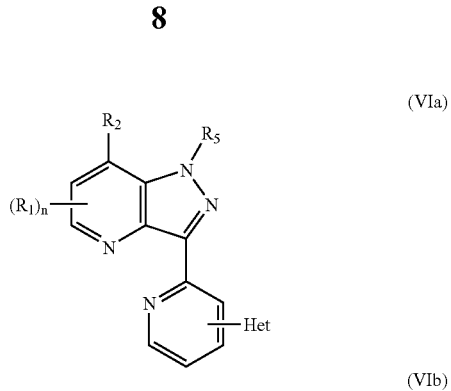

(VIa)

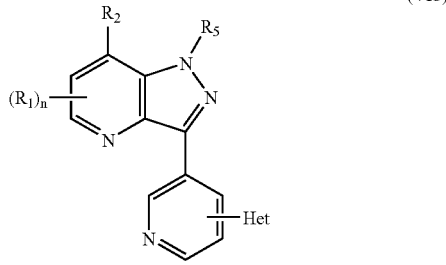

(VIb)

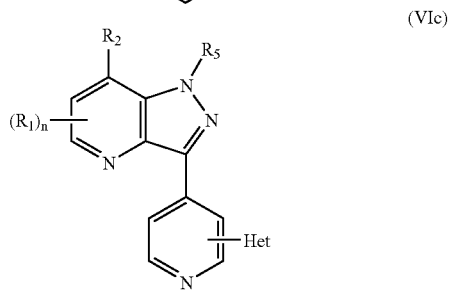

(VIc)

In further embodiments of the invention Ar is pyridyl which is bonded to the pyrazolopyridine core through carbon atom numbers 2, 3 or 4 of the pyridyl ring, as shown in the following structures (VIIa, VIIb and VIIc), respectively, and in which m is an integer 1-3 inclusive and each $R_6$ is independently $C_1$-$C_6$ alkyl, substituted $C_1$-$C_6$ alkyl, $C_1$-$C_6$ alkoxy or halogen:

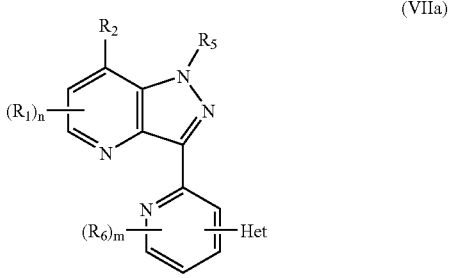

(VIIa)

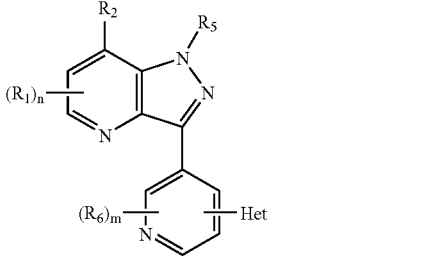

(VIIb)

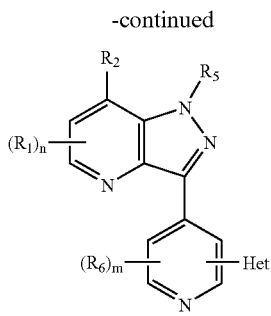

(VIIc)

In further embodiments of the invention Het is heterocyclyl or substituted heterocyclyl, wherein heterocyclyl is exemplified without limitation by pyrrolyl, pyrazolyl, imidazolyl, furazanyl, pyridyl, pyridinyl, pyridazinyl, pyrimidinyl, pyrazinyl and tetrahydroindolone.

The compounds of the present invention may generally be utilized as the free base. Alternatively, the compounds of this invention may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all pharmaceutically acceptable salt forms.

In general, the compounds of structure (I) may be made according to the organic synthesis techniques known to those skilled in this field, as well as by the representative methods set forth in the Examples. For example, the synthesis of structure (I) may generally proceed according to the following Reaction Scheme 1 through Reaction Scheme 9, which schemes are presented for purposes of exemplification and not limitation.

Reaction Scheme 1

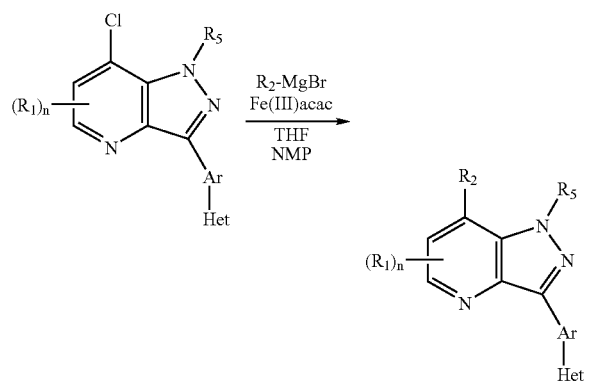

Alkylation at the 7-position of the 7-chloro pyrazolo[4,3-b]pyridine core proceeds via reaction of the alkylmagnesium bromide in the presence of iron(III) salts such as iron(III) acetylacetonate in tetrahydrofuran (THF) and N-methylpyrrolidone (NMP) (Fürstner et al, J. Am. Chem. Soc. 2002, 124, 13856-13863).

Reaction Scheme 2

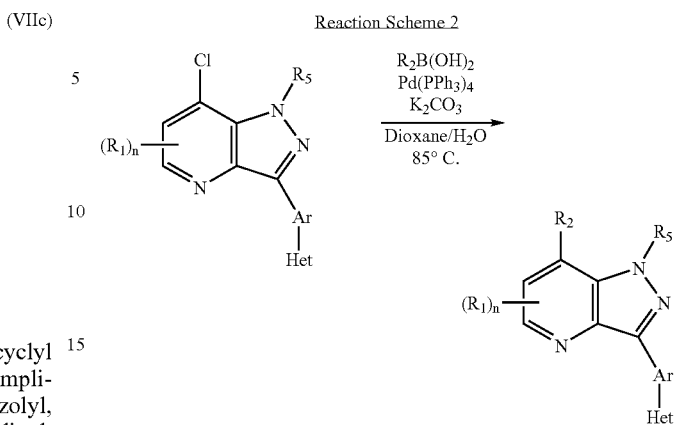

Substitution of chlorine at the 7-position of the 7-chloro pyrazolo[4,3-b]pyridine core by reaction with the boronic acid of aryl, substituted aryl, heteroaryl, or substituted heteroaryl, represented by $R_2B(OH_2)$ in Reaction Scheme 2 above, occurs in the presence of a suitable palladium catalyst such as tetrakis (triphenylphosphine)palladium(0) and a suitable base such as potassium carbonate at elevated temperature in a suitable solvent such as dioxane.

Reaction Scheme 3

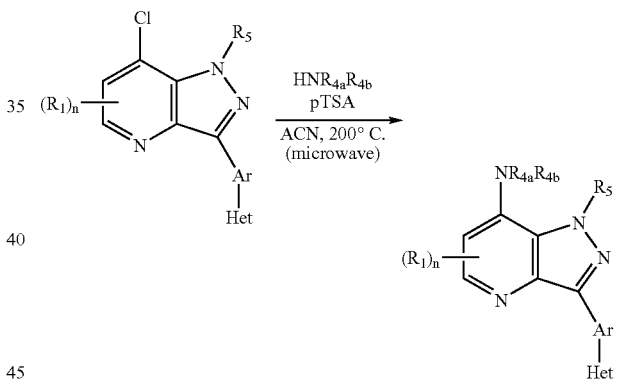

Substitution of chlorine at the 7-position of the 7-chloro pyrazolo[4,3-b]pyridine core by an amine, exemplified by $HNR_{4a}R_{4b}$ in Reaction Scheme 3 above, occurs in the presence of an acid such as p-toluenesulfonic acid in acetonitrile at elevated temperature.

Reaction Scheme 4

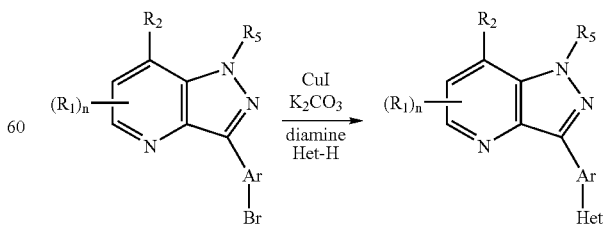

Substitution of aryl bromide or iodide by the nitrogen atom of an appropriate nitrogen heterocycle occurs in the presence of a copper catalyst such as copper(I) iodide, a diamine co-catalyst, and a base (Klapars et al, J. Am. Chem. Soc. 2002, 124, 7241-7428). Suitable diamines include N,N'-dimethylethylenediamine and trans-1,2-cyclohexanediamine. Suitable bases are potassium carbonate and tri-potassium phosphate.

Reaction Scheme 5

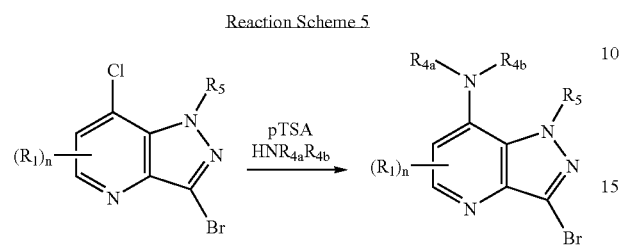

Substitution of chlorine by amine at the 7-position of the 3-bromo-7-chloro-1H-pyrazolo[4,3-b]pyridine core occurs at elevated temperature in the presence of p-toluenesulfonic acid.

Reaction Scheme 6

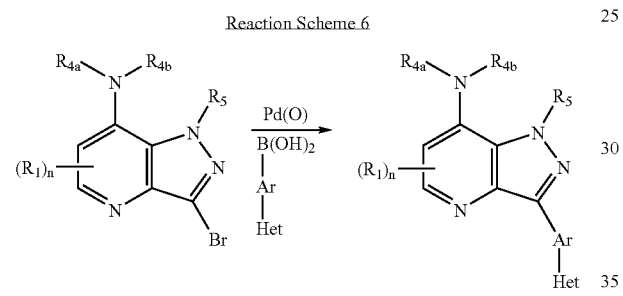

Palladium-catalyzed cross coupling of organic halides with organoboron derivatives can be employed to achieve substitution at the 3-position of the pyrazolo[4,3-b]pyridine Reaction Scheme 7

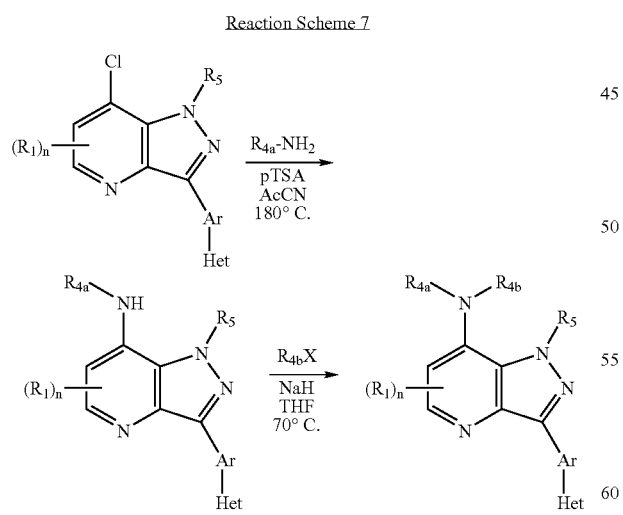

Substitution of amine for chlorine at the 7-position of the pyrazolo[4,3-b]pyridine core occurs at elevated temperature in the presence of p-toluenesulfonic acid to afford the amine in a process similar to that described for Scheme 3. The intermediate secondary amine can be converted to a tertiary amine by reaction with an alkyl halide $R_{4b}X$ in Reaction Scheme 7 above in the presence of a base such as NaH in an inert solvent such as THF or DMF.

Reaction Scheme 8

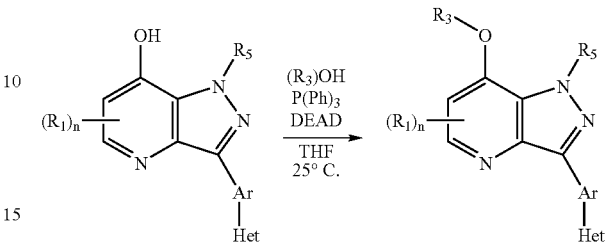

The 7-hydroxypyrazolo[4,3-b]pyridine core can be alkylated with a primary or secondary alcohol, exemplified by $(R_3)OH$ in the Reaction Scheme above, under Mitsunobu conditions employing a phosphine such as triphenylphosphine and an azodicarboxylate such as diethylazodicarboxylate in an inert anhydrous solvent such as THF or toluene.

Reaction Scheme 9

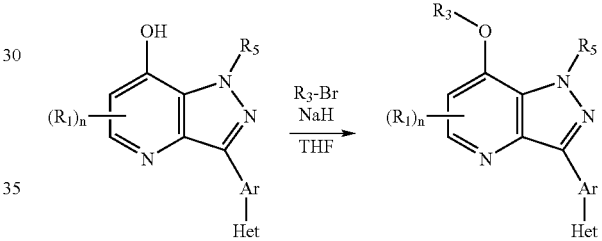

The 7-hydroxypyrazolo[4,3-b]pyridine core can be alkylated with a primary or secondary alkyl halide, exemplified by $R_3Br$ in Reaction Scheme 9 above, using an appropriate base such as NaH and a suitable anhydrous solvent such as THF or DMF at elevated temperature to afford the alkoxy compound.

Reaction Scheme 10

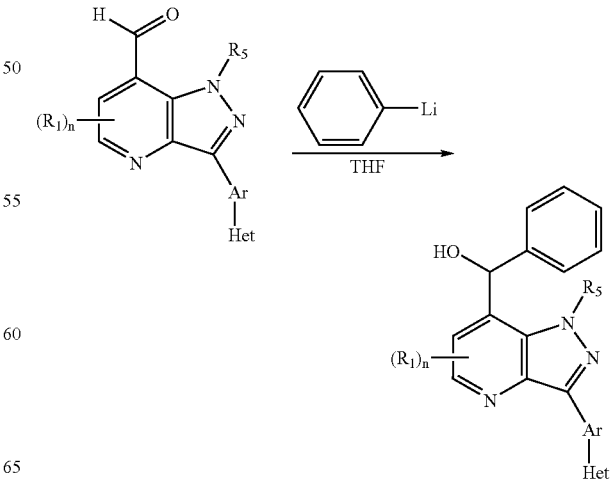

Phenyllithium reacts with the aldehyde functionality at the 7-position of the pyrazolo[4,3-b]pyridine core to give the phenyl-(1H-pyrazolo[4,3-b]pyridin-7-yl)-methanol.

The effectiveness of a compound as a CRF receptor antagonist may be determined by various assay methods. Suitable CRF antagonists of this invention are capable of inhibiting the specific binding of CRF to its receptor. A compound of structure (I) may be assessed for activity as a CRF antagonist by one or more generally accepted assays for this purpose, including, but not limited to, the assays disclosed by DeSouza et al. (*J. Neuroscience* 7:88, 1987) and Battaglia et al. (*Synapse* 1:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (e.g., [$^{125}$I]tyrosine-CFR) to its receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)).

With reference to CRF receptor binding affinities, CRF receptor antagonists of this invention typically have a $K_i$ of less than 10 µM. In one embodiment of this invention, a CRF receptor antagonist has a $K_i$ of less than 1 µM. In another embodiment, a CRF antagonist of this invention has a $K_i$ of less than 0.25 µM (i.e., 250 nM). As set forth in greater detail below, the $K_i$ values may be assayed by the methods set forth in Example 20.

CRF receptor antagonists of the present invention may demonstrate activity at the CRF receptor site, and may be used as therapeutic agents for the treatment of a wide range of disorders or illnesses including endocrine, psychiatric, and neurological disorders or illnesses. More specifically, CRF receptor antagonists of the present invention may be useful in treating physiological conditions or disorders arising from the hypersecretion of CRF. Because CRF is believed to be an important neurotransmitter that activates and coordinates the endocrine, behavioral and automatic responses to stress, CRF receptor antagonists of the present invention can be used to treat neuropsychiatric disorders. Neuropsychiatric disorders which may be treatable by CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists also may be useful in treating stress-induced immune suppression associated with various diseases states, as well as stroke. Other uses of CRF antagonists of this invention may include treatment of inflammatory conditions (such as rheumatoid arthritis, uveitis, asthma, inflammatory bowel disease and G.I. motility), pain, Cushing's disease, infantile spasms, epilepsy and other seizures in both infants and adults, as well as substance abuse and withdrawal (e.g., alcoholism).

In another embodiment, the present invention provides pharmaceutical compositions containing one or more CRF receptor antagonists of the invention. For the purposes of administration to an animal (e.g., a mammal) the compounds of the present invention may be formulated as pharmaceutical compositions. Pharmaceutical compositions of the present invention comprise a CRF receptor antagonist of the present invention (i.e., a compound of structure (I)) and a pharmaceutically acceptable carrier and/or diluent. The CRF receptor antagonist is present in the composition in an amount which is effective to treat a particular disorder, that is, in an amount sufficient to achieve CRF receptor antagonist activity and preferably with acceptable toxicity to the patient. In one embodiment, the pharmaceutical compositions of the present invention may include a CRF receptor antagonist in an amount from 0.1 mg to 250 mg per dosage depending upon the route of administration, and more specifically from 1 mg to 60 mg. In other embodiments, the dosage may be, for example, 5 mg, 10 mg, 15 mg or 20 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions also may be formulated as pills, capsules, granules, or tablets which contain, in addition to a CRF receptor antagonist, common additives such as diluents, dispersing and surface active agents, binders, and lubricants. One skilled in this art may further formulate the CRF receptor antagonist in an appropriate manner, and in accordance with accepted practices, such as those disclosed in *Remington's Pharmaceutical Sciences*, Gennaro, Ed., Mack Publishing Co., Easton, Pa. 1990.

In addition, prodrugs are also included within the context of this invention. Prodrugs are any covalently bonded carriers that release a compound of structure (I) in vivo when such prodrug is administered to a patient. Prodrugs generally are prepared by modifying functional groups in a way such that the modification is cleaved, either by routine manipulation or in vivo, yielding the parent compound.

The compounds of structure (I) may have chiral centers and may occur as racemates, racemic mixtures and as individual enantiomers or diastereomers. All such isomeric forms are included within the present invention, including mixtures thereof. Furthermore, crystalline forms of the compounds of structure (I) may exist as polymorphs, which are included in the present invention. In addition, compounds of structure (I)

may form solvates with water or other organic solvents. Such solvates are similarly included within the scope of this invention.

In another embodiment, the present invention provides a method for treating a variety of disorders or illnesses, including endocrine, psychiatric and neurological disorders or illnesses. Such methods include administering a compound of the present invention to a mammal (e.g., a person) in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules, as well as liquids, syrups, suspensions, and emulsions. These compositions also may include flavorants, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

In another embodiment, the present invention permits the diagnostic visualization of specific sites within the body by the use of radioactive or non-radioactive pharmaceutical agents Use of a compound of the present invention may provide a physiological, functional, or biological assessment of a patient or provide disease or pathology detection and assessment. Radioactive pharmaceuticals are employed in scintigraphy, positron emission tomography (PET), computerized tomography (CT), and single photon emission computerized tomography (SPECT). For such applications, radioisotopes are incorporated of such elements as iodine (I) including $^{123}$I (PET), $^{125}$I (SPECT), and $^{131}$I, technetium (Tc) including $^{99}$Tc (PET), phosphorus (P) including $^{31}$P and $^{32}$P, chromium (Cr) including $^{51}$Cr, carbon (C) including $^{11}$C, fluorine (F) including $^{18}$F, thallium (Tl) including $^{201}$Tl, and like emitters of positron and ionizing radiation. Non-radioactive pharmaceuticals are employed in magnetic resonance imaging (MRI), fluoroscopy, and ultrasound. For such applications, isotopes are incorporated of such elements as gadolinium (Gd) including $^{153}$Gd, iron (Fe), barium (Ba), manganese (Mn), and thallium (Tl). Such entities are also useful for identifying the presence of particular target sites in a mixture and for labeling molecules in a mixture.

As mentioned above, administration of a compound of the present invention may be useful for treating a wide variety of disorders or illnesses. In particular, compounds of the present invention may be administered to a mammal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, pain, Cushing's disease, infantile spasms, epilepsy, and substance abuse or withdrawal.

The following examples are provided for purposes of illustration and not for purposes of limitation.

EXAMPLES

The CRF receptor antagonists of this invention may be prepared by the methods disclosed in the Examples. Example 20 presents a method for determining the receptor binding affinity, and Example 21 discloses an assay for screening compounds of this invention for CRF-stimulated adenylate cyclase activity.

Abbreviations:
  LAH: Lithium aluminum hydride
  DCM: Dichloromethane
  DMSO: Dimethyl sulfoxide
  EAA: Ethyl acetoacetate
  LC-MS: liquid chromatography-mass spectroscopy
  NaBH(OAc)$_3$: Sodium Triacetoxyborohydride
  Pd—C: Palladium (10%) on Carbon
  TFA: Trifluoroacetic acid
  acac: acetylacetonate
  MDA: Malondialdehyde bis-dimethylacetal
  MEEA: (2-methoxyethyl)ethylamine Prep. HPLC-MS
  Gilson HPLC-MS equipped with Gilson 215 auto-sampler/fraction collector, an UV detector and a ThermoFinnigan AQA Single QUAD Mass detector (electrospray);
  HPLC column: BHK ODS-O/B, 5μ, 30×75 mm
  HPLC gradients: 35 mL/min, 10% acetonitrile in water to 100% acetonitrile in 7 min, maintaining 100% acetonitrile for 3 min.

Analytical Method 1—High Performance Liquid Chromatography (HPLC-MS)
  Column: Phenomenex SynergiMAX-RP, 4 micron, 2×50 mm;
  Mobile phase: A=water, 0.025% TFA; B=acetonitrile, 0.025% TFA;
  Gradient: 5% B/95% A to 95% B/5% A over 13 min, then hold 2.5 min;
  Flow rate: 1.0 mL/min;
  UV wavelength: 220 nm and 254 nm.

Analytical Method 2—Supercritical Fluid Chromatography (SFC)
  Platform: Berger FCM1200 SFC pump, Agilent Diode Array Detector, Agilent Model 220 Microplate autosampler, Agilent Model 1946 MSD (APCI interface);
  Column: Berger Pyridine 60A, 4 micron, 3×150 mm;
  Solvents: SFC Grade CO$_2$, Optima-grade methanol with 1.5% water and 0.025% ethanesulfonic acid;
  Flow rate: 4.0 mL/min, 120 Bar backpressure;
  Gradient: 5-55% methanol/CO$_2$ in 2.4 min.
  Retention times ($t_R$) reported for all compounds employed Analytical Method 1 with the exception of Compound 13-1 which employed Analytical Method 2.

Example 1

SYNTHESIS OF REAGENTS 3-BROMO-7-CHLORO-5-METHYL-1H-PYRAZOLO[4,3-b]PYRIDINE AND 7-BENZYLOXY-3-BROMO-5-METHYL-1H-PYRAZOLO[4,3-b]PYRIDINE

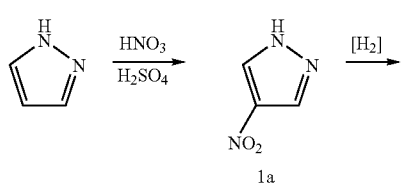

1a

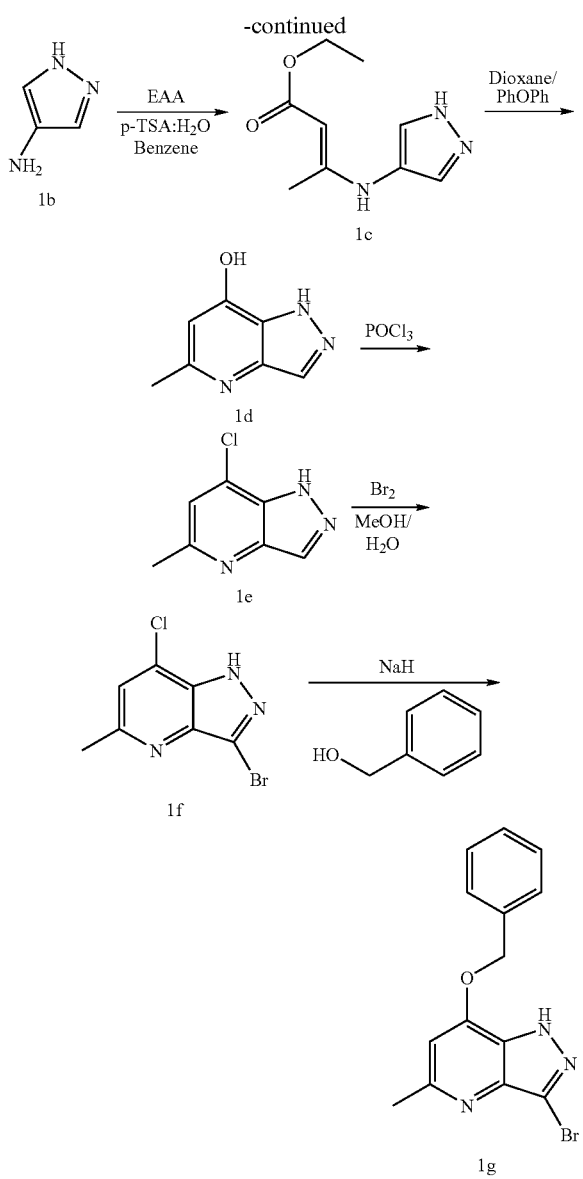

Step 1A:

Pyrazole (30.0 g, 441 mmol) was added portionwise to sulfuric acid (220 mL, 97%) in an ice-bath. The mixture was heated at 55° C. and nitric acid (30 mL, 70%, 0.5 mol) was added slowly. The reaction mixture was stirred at 55° C. for 3 hours, cooled down, poured into ice-water (600 mL) and neutralized with 6N NaOH solution (pH=7). The reaction mixture was extracted with ethyl acetate (5×150 mL). The organic phases were combined, washed with water (100 mL) and brine (100 mL), dried with sodium sulfate, filtered and concentrated by vacuum to afford compound 1a as a white solid (37.0 g, 326 mmol, 74%); GC/MS: m/z=113 (100%).

Compound 1a (15.0 g, 133 mmol) was added to a suspension of palladium on carbon 10% (7.0 g, 6.65 mmol) in ethanol (100 mL). The mixture was shaken for 3 hours under hydrogen pressure (40 psi) at room temperature. The catalyst was removed by filtration through a pad of CeliteX and the solvent was evaporated. Compound 1b was obtained as a burgundy oil (10.5 g, 126 mmol, 95%) which was used in the following step without purification; GC/MS: m/z=83 (100%).

Step 1C:

A solution of 1b (10.5 g, 126 mmol), ethylacetoacetate (18.0 g, 140 mmol) and a catalytic amount of p-toluenesulfonic acid monohydrate (1.3 g, 6.65 mmol, 5%) in benzene (100 mL) was refluxed with a Dean-Stark trap for 1 hour. Solvents were removed under vacuum, and the imine was purified by running through a short silica chromatography column to afford compound 1c as a tan solid after evaporation of solvent (22.4 g, 125 mmol, 91%); GC/MS: m/z=195 (100%).

Step 1D:

Compound 1c (7.03 g, 35.9 mmol) was added to a boiling solution of dioxane (30 mL) and diphenyl ether (30 mL). The mixture was heated until solid formed (5 min). The reaction mixture was continued at heat for 2 more min. After cooling down at room temperature, diethyl ether (300 mL) was added, and the reaction mixture was stirred for 15 min. The solid was rinsed with diethyl ether. Compound 1d was obtained as a tan crystalline solid (5.09 g, 34.1 mmol, 95%); LC/MS: [M+H]=150.0.

Step 1E:

Compound 1d (4.58 g, 30.7 mmol) in phosphorus oxychloride (30 mL) was heated at 110° C. for 30 min. After cooling down at room temperature, the reaction mixture was poured onto ice, and the pH was adjusted with NaOH solution (6N) to pH=5. The solid was collected with filtration and the mother aqueous layer was extracted with ethyl acetate (3×250 mL). The aforementioned solid was dissolved in the combined organic phases, washed with a brine solution (1×250 mL), dried with sodium sulfate, filtered and concentrated. The concentrate was purified by running through a short silica gel chromatography column to afford compound 1e as a pale yellow solid (4.50 g, 26.8 mmol, 87%); GC/MS: m/z=167 (100%); LC/MS: [M+H]=168.

Step 1F:

Compound 1e (600 mg, 3.58 mmol) was dissolved in a mixture of water/methanol (12 mL/12 mL) in an ice-bath. A solution of bromine (629 mg, 3.94 mmol) in a solution of H$_2$O/MeOH 1 mL/1 mL was added dropwise to the cooled mixture. After 10 min, the solution was clearer and the LC/MS showed no more chloro compound. The reaction mixture was concentrated to remove the MeOH. The reaction mixture was extracted with ethyl acetate (3×50 mL). The organic phases were combined, washed with a brine solution (1×100 mL) and dried with sodium sulfate, filtered and concentrated by vacuum. Compound 1f was obtained as a pale yellow solid. GC/MS: m/z=245, 247 (100%); LC/MS: [M+H]=246.2.

Step 1G:

To compound 1f (4.9 g, 19 mmol) in 30 mL anhydrous dioxane was added NaH (1.0 g of 60% solution in mineral oil) followed by benzyl alcohol (2.3 mL) with reflux for 12 hr. The reaction was quenched with H$_2$O and neutralized with 6N HCl. The reaction mixture was extracted with ethyl acetate and the combined organic layers were dried over MgSO$_4$ and concentrated to afford after column chromatography (1:1 ethyl acetate:hexane) compound 1g (3.5 g, 56%); LC/MS: [M+H]=332.1.

Example 2

SYNTHESIS OF REAGENTS 1-(4-BROMO-3-METHYLPHENYL) PYRAZOLE AND 2-METHYL-4-(PYRAZOL-1-YL)PHENYLBO-RONIC ACID PINACOL ESTER

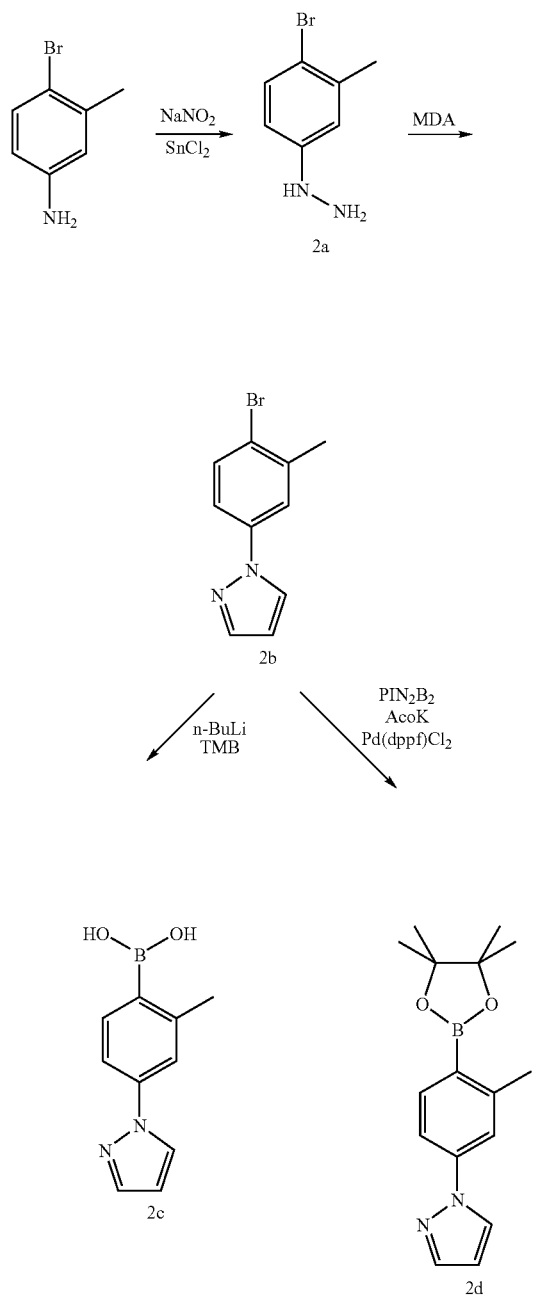

Step 2A:

4-Bromo-3-methylaniline (10.2 g) was suspended in 6N HCl (85 mL) and cooled to 0° C. A solution of sodium nitrite (4 g in 40 mL H$_2$O) was added over 10 min. The reaction was stirred for 15 min at 0° C. followed by the addition of stannous chloride dihydrate (36 g in 25 mL 12N HCl). The reaction was stirred for 2 hours at 0° C. The reaction was filtered, and the filter cake was washed with cold H$_2$O to afford 4-bromo-3-methylphenylhydrazine hydrochloride (compound 2a, 20 g) as a tan solid.

Step 2B:

The compound resulting from Step 2A (20 g) was suspended in 50 mL ethanol. Malondialdehyde bis-dimethylacetal (11.0 mL, 67 mmol) was added and the reaction was heated to 85° C. for 2 hours. The reaction mixture was neutralized with sodium bicarbonate and extracted by washing with DCM. The combined organic layers were dried over magnesium sulfate and concentrated. The residue was taken up in ethyl acetate, and the mixture was filtered through a pad of Celite®. The filtrate was evaporated, and the oily residue was purified by column chromatography (1:1 ethyl acetate: hexanes) to afford 1-(4-bromo-3-methylphenyl)pyrazole (compound 2b, 9.6 g, 73%) as an amber oil; LC/MS: [M+H] =238.8.

Step 2C:

n-Butyllithium (7.9 mL of a 2.5 M solution in hexanes, 20 mmol) was added to a solution of compound 2b (4.7 g, 20 mmol) in 100 mL THF at −78° C. The mixture was allowed to warm to −25° C. over 1 hr, then the mixture was cooled to −78° C. Trimethylborate (3.4 mL, 30 mmol) was added and the reaction was allowed to warm to RT. Hydrochloric acid (1N, 100 mL) was then added and the mixture was stirred for 16 hr. The pH of the aqueous layer was adjusted to 3-4 using sodium hydroxide and sodium dihydrogen phosphate solution, then the mixture was extracted with ethyl acetate. The organic layer was concentrated, then the residue was partitioned between ether and 0.5 N sodium hydroxide solution. The aqueous layer was extracted with two additional portions of ether and was then acidified to pH 3-4 using concentrated hydrochloric acid. The mixture was extracted with ethyl acetate, and the combined ethyl acetate extracts were dried over sodium sulfate, filtered, and evaporated to afford 2-methyl-4-(pyrazol-1-yl)phenylboronic acid (compound 2c, 3.5 g) as an amber gum.

Step 2D:

To a solution of compound 2b (2.0 g in 15 mL dioxane) was added bis(pinacolato)diboron (2.4 g), potassium acetate (2.4 g) and 1,1'-bis(diphenylphosphino) ferrocene dichloropalladium (II) (500 mg). The reaction was heated to 85° C. for 12 hours. The reaction mixture was filtered through a pad of Celite® and the filter cake washed with ethyl acetate. The filtrate was concentrated to a brown liquid which was purified by column chromatography (20% ethyl acetate:hexanes) to afford 2-methyl-4-(pyrazol-1-yl)phenylboronic acid pinacol ester (compound 2d, 1.8 g, 75%) as a yellow oil; LC/MS: [M+H]=285.0.

Also prepared by the methods above giving compound 2d were the following compounds: 2-methoxy-4-(pyrazol-1-yl) phenylboronic acid pinacol ester (compound 2e); 2-chloro-4-(pyrazol-1-yl)phenylboronic acid pinacol ester (compound 2f); and 4-(pyrazol-1-yl)-2-(trifluoromethyl)phenylboronic acid pinacol ester (compound 2g).

Example 3

SYNTHESIS OF REAGENTS 7-BENZYLOXY-1,5-DIMETHYL-3-(2-METHYL-4-PYRAZOL-1-YL-PHENYL)-1H-PYRAZOLO[4,3-b]PYRIDINE AND 1,5-DIMETHYL-3-(2-METHYL-4-PYRAZOL-1-YL-PHENYL)-1H-PYRAZOLO[4,3-b]PYRIDIN-7-OL

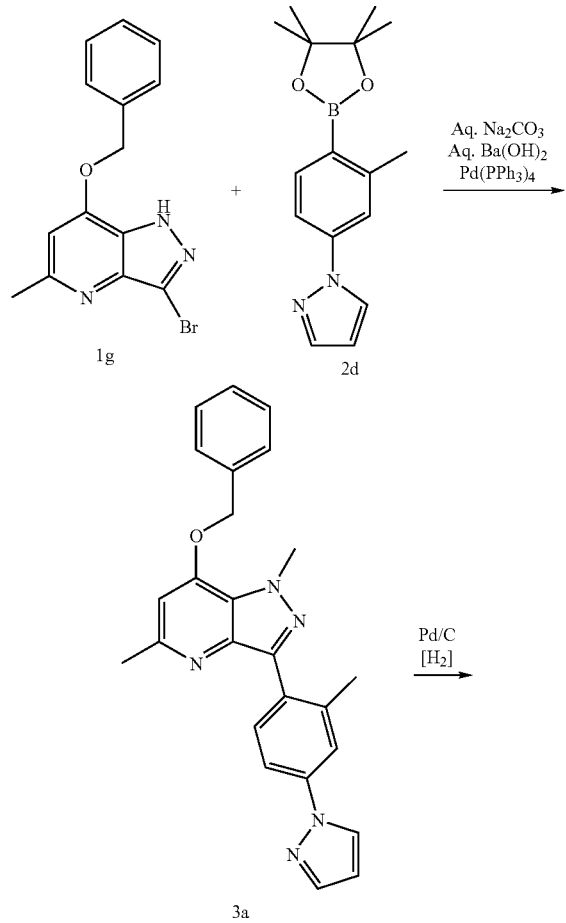

Step 3A:

To a solution of compound 1g (1.0 g in 5 mL toluene) was added ethanol (2 mL). To this mixture was added compound 2d (1.3 g) followed by aqueous sodium carbonate (3.5 mL of 2.0 M solution), saturated aqueous barium hydroxide (1 mL) and tetrakis(triphenylphosphine)palladium(0) (200 mg, 0.15 mmol). The reaction mixture was stirred and heated at 85° C. for 12 hours. The mixture was cooled and the organic phase was separated. The aqueous phase was washed with ethyl acetate (3×50 mL), and the combined organic extracts were dried over magnesium sulfate, filtered, and concentrated to a yellow oil which was purified by column chromatography (30% ethyl acetate:hexanes) to afford 7-benzyloxy-1,5-dimethyl-3-(2-methyl-4-pyrazol-1-yl-phenyl)-1H-pyrazolo[4,3-b]pyridine (compound 3a, 0.82 g, 67%) as an off white solid; LC/MS: [M+H]=411.2.

Also prepared by the method used for the preparation of compound 3a were the following compounds: 7-benzyloxy-3-[2-methoxy-4-(pyrazol-1-yl)phenyl]-1,5-dimethylpyrazolo[4,3-b]pyridine (compound 3b); 7-benzyloxy-3-[2-chloro-4-(pyrazol-1-yl)phenyl]-1,5-dimethylpyrazolo[4,3-b]pyridine (compound 3c); and 7-benzyloxy-3-[4-(pyrazol-1-yl)-2-(trifluoromethyl)phenyl]-1,5-dimethylpyrazolo[4,3-b]pyridine (compound 3d).

Step 3B:

To a solution of compound 3a (2.0 g in 30 mL ethanol) was added 10% palladium on carbon (0.3 g). The reaction was shaken for 2 hours under 40 psi hydrogen. The reaction mixture was filtered through a pad of Celite®, and the filter cake was washed with ethanol. The filtrate was concentrated to afford 1,5-dimethyl-3-(2-methyl-4-pyrazol-1-yl-phenyl)-1H-pyrazolo[4,3-b]pyridin-7-ol (compound 3e, 1.2 g, 77%) as an off white solid; LC/MS: [M+H]=319.0.

Also prepared by the methods exemplified in Example 3 were the following compounds: 7-hydroxy-3-[2-methoxy-4-(pyrazol-1-yl)phenyl]-1,5-dimethyl-pyrazolo[4,3-b]pyridine (compound 3f); 7-hydroxy-3-[2-chloro-4-(pyrazol-1-yl)phenyl]-1,5-dimethylpyrazolo[4,3-b]pyridine, using platinum oxide as catalyst in place of Pd/C (compound 3g); and 7-hydroxy-3-[4-(pyrazol-1-yl)-2-(trifluoromethyl)phenyl]-1,5-dimethylpyrazolo[4,3-b]pyridine (compound 3h).

Example 4

SYNTHESIS OF REAGENT 7-CHLORO-1,5-DIMETHYL-3-(2-METHYL-4-PYRAZOL-1-YL-PHENYL)-1H-PYRAZOLO[4,3-b]PYRIDINE

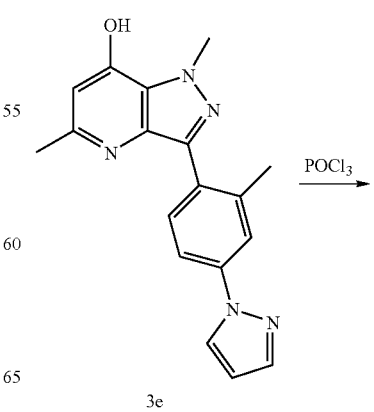

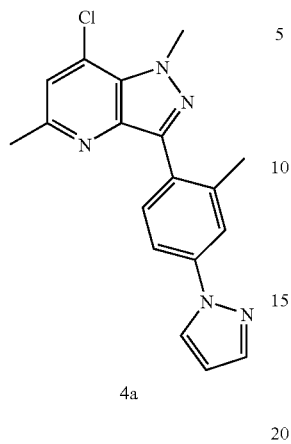

4a

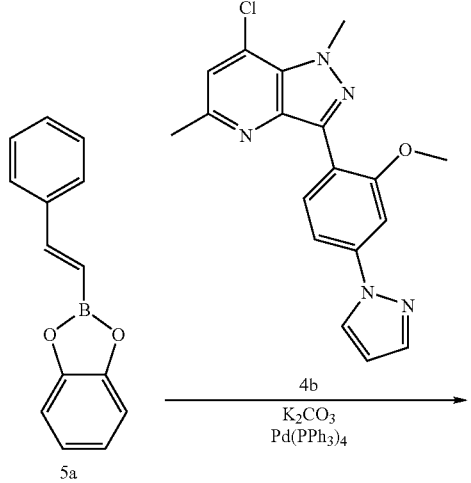

5a

Step 4A:

To a solution of compound 3e (1.0 g) in anhydrous acetonitrile (10 mL) was added phosphorous oxychloride (0.60 mL). The reaction was refluxed under nitrogen for 2 hours. The reaction mixture was cooled and quenched on ice with $H_2O$. The mixture was basified to pH 8 with sodium bicarbonate. The product was extracted with ethyl acetate (3×50 mL). The organic layers were combined, dried over magnesium sulfate and concentrated to afford 7-chloro-1,5-dimethyl-3-(2-methyl-4-pyrazol-1-yl-phenyl)-1H-pyrazolo[4,3-b]pyridine as a yellow oil. The compound was purified by silica gel chromatography, using 30% ethyl acetate/hexanes as eluent to provide 1.0 g (99%) of compound 4a as a white solid; LC/MS: [M+H]=338.2.

Also prepared by the method used for preparation of compound 4a were the following compounds: 7-chloro-3-[2-methoxy-4-(pyrazol-1-yl)phenyl]-1,5-dimethylpyrazolo[4,3-b]pyridine (compound 4b); 7-chloro-3-[2-chloro-4-(pyrazol-1-yl)phenyl]-1,5-dimethylpyrazolo[4,3-b]pyridine (compound 4c); 7-chloro-3-[4-(pyrazol-1-yl)-2-(trifluoromethyl)phenyl]-1,5-dimethylpyrazolo[4,3-b]pyridine (compound 4d); and 7-chloro-3-(4-bromo-2-methoxyphenyl)-1,5-dimethylpyrazolo[4,3-b]pyridine (compound 4e).

Example 5

SYNTHESIS OF REAGENT 7-FORMYL-3-[2-METHOXY-4-(PYRAZOL-1-YL)PHENYL]-1,5-DIMETHYLPYRAZOLO[4,3-B]PYRIDINE

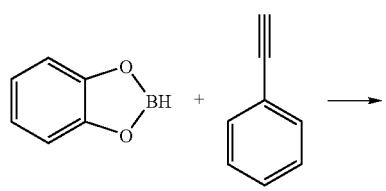

Step 5A:

Catecholborane (36 mL of a 1.0 M solution in THF, 36 mmol) was added to phenylacetylene (3.06 g, 30 mmol) and the mixture was heated to reflux under nitrogen for 2 hr. The cooled solution of 2-phenyl-ethenylboronic acid catechol ester (compound 5a) was used without further purification.

Step 5B:

Compound 5a (0.75 mL of the nominally 1.0 M solution, 0.75 mmol) was added via syringe to 7-chloro-3-[2-methoxy-4-(pyrazol-1-yl)phenyl]-1,5-dimethyl pyrazolo[4,3-b]pyridine (compound 4b, 200 mg, 0.57 mmol) under nitrogen and the mixture was evaporated to dryness. Dioxane (2 mL) and water (2 mL) were added, followed by potassium carbonate (157 mg, 1.14 mmol) and tetrakis (triphenylphosphine)palladium(0) (66 mg, 0.057 mmol). The mixture was stirred and heated to reflux for 6 hr and then was allowed to cool. Water (5 mL) was added and the mixture was extracted with ethyl acetate. The combined organic extracts were dried over sodium sulfate, concentrated, and the residue was chromatographed on silica gel using 1:2 hexanes/ethyl acetate to afford 7-(2-phenyl-1-ethenyl)-3-[2-methoxy-4-(pyrazol-1-yl)phenyl]-1,5-dimethylpyrazolo[4,3-b]pyridine (compound 5b, 201 mg) as a yellow oil.

Step 5C:

A stream of ozone in oxygen was passed through a solution of compound 5b (200 mg, 0.47 mmol) in 4:1 DCM/methanol (10 mL) at −78° C. Following consumption of starting material, the solution was sparged with nitrogen, and then dimethylsulfide (0.200 mL) was added and the mixture was allowed to warm to RT. After 1.5 hr, the solvent was evaporated and the residue was chromatographed on silica gel using 1:2 hexanes/ethyl acetate as eluent, providing compound 5c (149 mg) as a yellow solid.

Example 6

SYNTHESIS OF REAGENT 2-[2-(4-BROMO-2-METHOXY-PHENYL)-2-OXO-ETHYL]-ISOINDOLE-1,3-DIONE

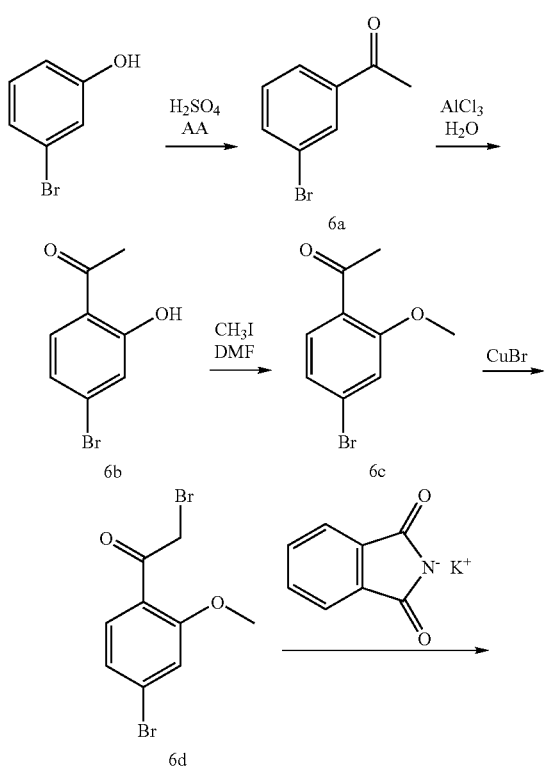

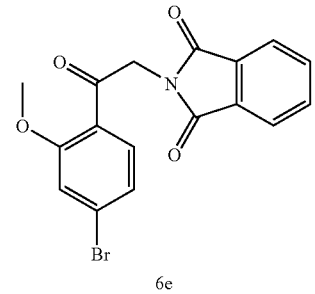

Step 6A:

Concentrated sulfuric acid (0.3 mL) was added to a stirred mixture of 3-bromophenol (26.2 g) and acetic anhydride (15 mL). An exothermic reaction took place, after which the mixture was allowed to cool to RT. Acetic acid and excess acetic anhydride were evaporated, and the residue was poured onto ice. The mixture was extracted with ether, and the combined ether extracts were washed with brine, then dried over magnesium sulfate and concentrated to afford 3-bromophenyl acetate (compound 6a, 31.6 g) as an amber oil.

Step 6B:

A mixture of compound 6a (31.6 g) and aluminum chloride (35 g) was heated at 160-170° C. for 3 hours. The mixture was allowed to cool to RT then was slurried with DCM, and the mixture was poured onto ice. The mixture was stirred until two clear liquid phases were obtained (12 hr). The layers were separated, then the aqueous layer was extracted once with DCM, and the combined organic layers were dried over sodium sulfate, filtered, and evaporated to afford 1-(4-bromo-2-hydroxyphenyl)-1-ethanone (compound 6b, 32.6 g) as an amber oil.

Step 6C:

Iodomethane (11.2 mL) was added to a mixture of compound 6b (32.6 g), DMF (100 mL), and potassium carbonate (62.5 g) at 0° C. The mixture was stirred and allowed to warm to RT over 2 hr. Water (200 mL) was added, and the mixture was extracted with ethyl acetate. The combined organic extracts were dried over sodium sulfate, filtered, and evaporated to afford 1-(4-bromo-2-methoxyphenyl)-1-ethanone (compound 6c, 33.1 g) as a tan solid.

Step 6D:

Cupric bromide (64.5 g, 223 mmol) was added to a solution of compound 6c in 500 mL ethyl acetate. The mixture was stirred and heated to reflux for 2 hr. The cooled reaction mixture was filtered and poured onto ice, and the mixture was neutralized with solid sodium bicarbonate. The layers were separated and the aqueous layer was extracted once with ethyl acetate. The combined organic layers were washed once with aqueous sodium thiosulfate, dried over sodium sulfate, filtered, and concentrated to provide 2,4'-dibromo-2'-methoxy-acetophenone (compound 6d, 43.5 g) as a tan solid.

Step 6E:

A solution of compound 6d (43.5 g) in anhydrous DMF (150 mL) was cooled to 5° C. To this solution was added potassium phthalimide (26.1 g, 141 mmol). After 5 min the cooling bath was removed and the reaction was allowed to stir at RT for 3 hr. The solvent was evaporated under vacuum to provide a tan solid. The solid was rinsed with 4:1 DCM/methanol and then water. The filter cake was slurried in toluene and evaporated to dryness to afford 4'-bromo-2'-methoxy-2-(phthalimido)acetophenone (compound 6e, 39 g) as a tan solid.

Example 7

Alternative Synthesis of 7-hydroxy-3-[2-methoxy-4-(pyrazol-1-yl)phenyl]-1,5-dimethyl-pyrazolo[4,3-b]pyridine

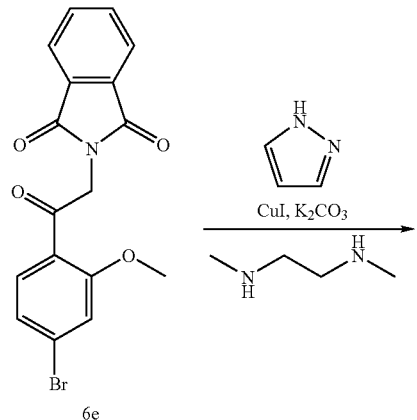

6e

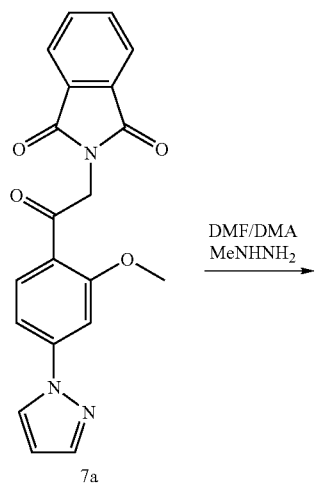

7a

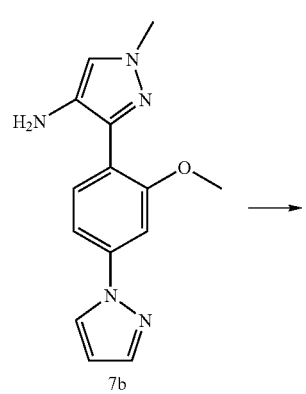

7b

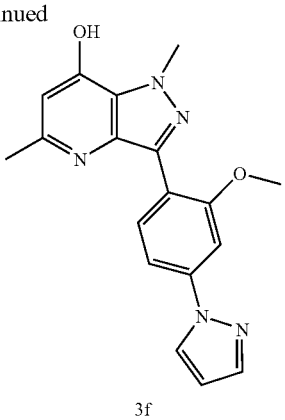

3f

Step 7A:

A suspension of compound 6e (18.4 g, 49 mmol), cuprous iodide (1.87 g, 9.8 mmol), pyrazole (6.7 g, 98 mmol), and potassium carbonate (20.4 g, 148 mmol) in anhydrous dioxane (150 mL) was sparged with nitrogen for 5 min. N,N'-dimethylethylene diamine (1.06 mL, 9.8 mmol) was added via syringe and the reaction vessel was sealed then heated to 105° C. with stirring for 29 hr. Upon cooling, the reaction mixture was filtered through Celite®, and the filter cake was rinsed with 500 mL DCM. The combined filtrates were evaporated to provide 29 g of a green solid, which was triturated with DCM to provide 11 g of 2-[2-(2-methoxy-4-pyrazol-1-yl-phenyl)-2-oxo-ethyl]-isoindole-1,3-dione (compound 7a) as a tan solid. This product contained approximately 15% of the starting bromide by LC/MS analysis and was used without further purification.

Step 7B:

A mixture of the compound resulting from Step 7A (11 g, 30 mmol), DMF (10 mL), and DMF dimethylacetal (8.1 mL, 61 mmol) was heated in a 125° C. bath with a gentle nitrogen purge for 1.5 hr. Additional DMF dimethylacetal (4.0 mL, 30 mmol) was added and heating was continued for 2 hr. The mixture was cooled then evaporated to dryness under vacuum to provide a tan solid. To this solid was added methylhydrazine (4.1 mL, 77 mmol) in absolute ethanol (100 mL), and the reaction mixture was refluxed for 3 hr. The solvent was evaporated and the resulting solid was washed with 3:1 ether/ethanol. The combined filtrates were evaporated to provide an aminopyrazole mixture (9.8 g) as a brown oil. The ratio of the two pyrazole isomers was judged to be 3:2 by $^1$H NMR integration of the pyrazole methyl signals.

Step 7C:

The compound resulting from step 7B (9.8 g, 36 mmol), ethylacetoacetate (5.1 mL, 40.0 mmol) and p-toluenesulfonic acid hydrate (1.0 g, 5 mmol) were suspended in toluene (150 mL) and the mixture was refluxed with azeotropic removal of water using a Dean-Stark trap. After 1.5 hr the mixture was allowed to cool and evaporated to dryness. The residue was suspended in diphenylether (40 mL) and added over 45 min to 20 mL of diphenylether (initial temperature 255° C.) keeping the temperature above 220° C. When the addition was complete, the mixture was allowed to cool to RT then was poured into 250 mL hexanes. The resulting precipitate was collected and washed with hexanes. The resulting compound was purified by silica gel chromatography using 4% methanol in DCM as eluent. Trituration of the partially purified solid product with ethyl acetate provided 7-hydroxy-3-[2-methoxy-4-(pyrazol-1-yl)phenyl]-1,5-dimethyl-pyrazolo[4,3b]pyridine (compound 3f, 3.75 g) as a brown solid.

Also prepared by the method described above for preparation of compound 3f was 7-hydroxy-3-]4-bromo-2-methoxyphenyl]1,5-dimethylpyrazolo[4,3-b]pyridine (compound 7c) using compound 6e as starting material and omitting Step 7A from the protocol.

Example 8

SYNTHESIS OF 7-ISOBUTYL-3-(2-METHOXY-4-PYRAZOL-1-YL-PHENYL)-1,5-DIMETHYL-1H-PYRAZOLO[4,3-B]PYRIDINE

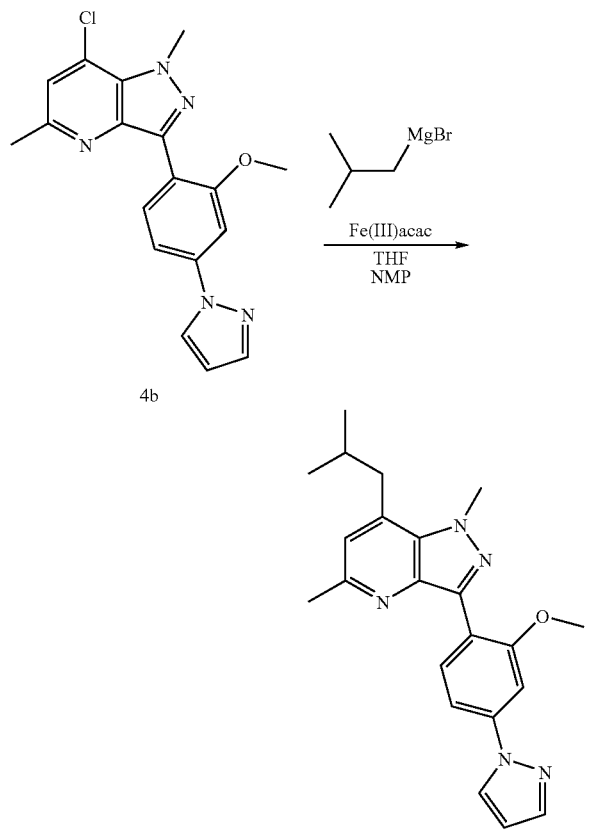

TABLE 1

| Cmpd | R₂ | MW | MS | $t_R$ |
|---|---|---|---|---|
| 8-1 | isobutyl | 375.47 | 376.3 | 5.15 |
| 8-2 | isopropyl | 361.45 | 362.3 | 4.67 |
| 8-3 | sec-butyl | 375.47 | 376.3 | 5.09 |

Example 9

SYNTHESIS OF 7-(2,4-DIMETHOXY-PHENYL)-3-(2-METHOXY-4-PYRAZOL-1-YL-PHENYL)-1,5-DIMETHYL-1H-PYRAZOLO[4,3-b]PYRIDINE

Step 8A:

Isobutylmagnesium bromide (0.6 mL of a 2.0 M solution) in ether was added to a suspension of compound 4b (85 mg, 0.24 mmol) and iron(III)acetylacetonate (60 mg, 0.18 mmol) in 0.6 mL THF and 0.15 mL NMP at 0° C. The mixture was allowed to warm to RT and was stirred for 3 hr. Aqueous ammonium chloride was added, and the mixture was extracted with ethyl acetate. The combined organic layers were dried over sodium sulfate, concentrated, and the residue was chromatographed on silica gel using 2:1 hexanes/ethyl acetate as eluent to give compound 8-1 (67 mg) as a tan solid. The hydrochloride salt (68 mg, tan powder) was prepared by adding 2 eq of ethereal HCl to a solution of the free base in DCM/ether, followed by evaporation of solvents.

Using the appropriate alkylmagnesium halide in place of isobutylmagnesium bromide in Step 8A, the compounds in the following table were synthesized:

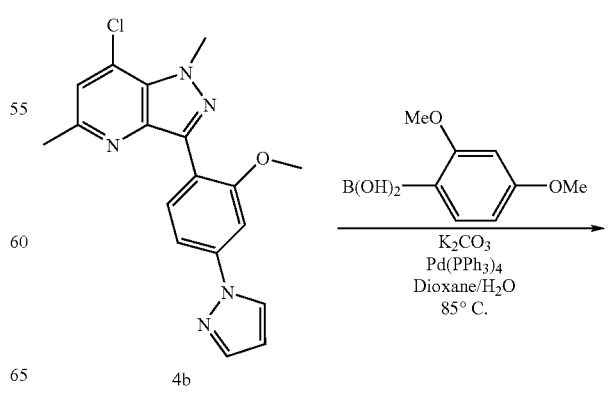

-continued

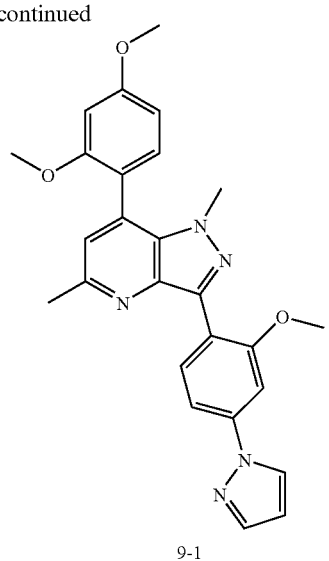

9-1

Step 9A:

To compound 4b (50 mg, 0.14 mmol) in dioxane (0.5 mL) was added 0.25 mL H₂O. To the mixture was added 2,4-dimethoxyphenylboronic acid (31 mg, 0.17 mmol) followed by potassium carbonate (30 mg, 0.22 mmol) and tetrakis(triphenylphosphine)palladium(0) (10 mg, 0.0017 mmol). The mixture was stirred and heated to 85° C. overnight. The reaction mixture was filtered and purified by HPLC MS to afford compound 9-1 (30.5 mg) as the TFA salt.

Using the appropriate boronic acid or boronate ester in place of 2,4-dimethoxyphenylboronic employed in Step 9A, the compounds in the following table were synthesized:

TABLE 2

| Cmpd | R₂ | MW | MS | $t_R$ |
|---|---|---|---|---|
| 9-1 | 2,4-dimethoxyphenyl | 455.52 | 456.0 | 5.507 |
| 9-2 | 2-methoxyphenyl | 425.49 | 426.0 | 5.57 |
| 9-3 | 3-methoxyphenyl | 425.49 | 426.4 | 5.799 |
| 9-4 | 2-fluoro-3-methoxyphenyl | 443.48 | 444.0 | 5.934 |
| 9-5 | 2-fluoropyridin-3-yl | 414.44 | 414.9 | 5.454 |
| 9-6 | 4-fluoro-2-methoxyphenyl | 443.48 | 444.0 | 5.706 |

TABLE 2-continued

| Cmpd | R$_2$ | MW | MS | t$_R$ |
|---|---|---|---|---|
| 9-7 | 3-fluoro-2-methoxyphenyl | 443.48 | 444.0 | 5.79 |
| 9-8 | 4-cyanophenyl | 420.47 | 420.9 | 5.579 |
| 9-9 | 2,5-dimethoxypyrimidin-5-yl | 457.49 | 458.0 | 5.259 |
| 9-10 | 2-fluoro-6-methoxyphenyl | 443.48 | 444.0 | 5.788 |
| 9-11 | 3-(methoxycarbonyl)phenyl | 453.50 | 454.0 | 5.813 |
| 9-12 | 2-(methoxymethyl)phenyl | 439.52 | 440.1 | 5.436 |

1,5-Dimethyl-3-(2-methyl-4-pyrazol-1-yl-phenyl)-7-(4-methyl-pyridin-3-yl)-1H-pyrazolo[4,3-b]pyridine 9-13 was synthesized according to the same procedure using compound 4a and (4-methyl-3-pyridinyl)-boronic acid. LC/MS: [M+H]=394.8, t$_R$=4.65.

Example 10

SYNTHESIS OF ETHYL-(2-METHOXY-ETHYL)-{3-[2-METHOXY-4-(3-TRIFLUOROMETHYL-PYRAZOL-1-YL)-PHENYL]-1,5-DIMETHYL-1H-PYRAZOLO[4,3-B]PYRIDIN-7-YL}-AMINE

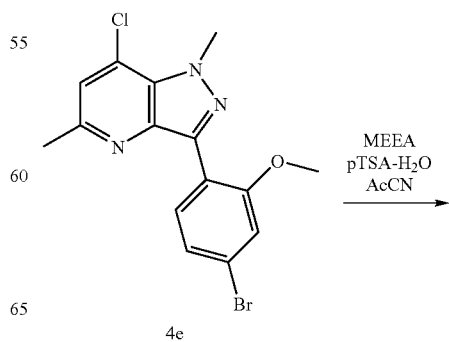

-continued

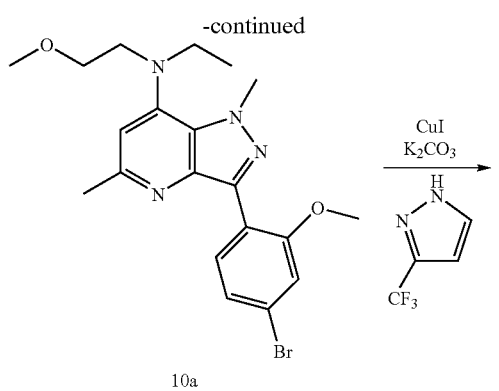

10a 10-1

Step 10A:

A mixture of compound 4e (1.07 g, 2.9 mmol), (2-methoxyethyl)ethylamine (1.43 mL, 11.7 mmol), pTSA hydrate (550 mg, 2.9 mmol), and acetonitrile (2 mL) was heated in a microwave oven for 60 min at 180° C. and then for 60 min at 195° C. The solvent was evaporated, and the residue was chromatographed on silica gel using 1:1 hexanes/ethyl acetate as eluent to afford compound 10a ([3-(4-Bromo-2-methoxy-phenyl)-1,5-dimethyl-1H-pyrazolo[4,3-b]pyridin-7-yl]-ethyl-(2-methoxy-ethyl)-amine) as an oil (1.1 g).

Step 10B:

Copper(I) iodide (6 mg, 0.03 mmol), potassium carbonate (62 mg, 0.45 mmol), and 3-(trifluoromethyl)pyrazole (41 mg, 0.3 mmol) were weighed into a 1 dram vial. A solution of compound 10a (65 mg, 0.15 mmol) in anhydrous dioxane (2 mL) was added followed by N,N'-dimethylethylenediamine (3 µl, 0.03 mmol). The vial was sealed with a Teflon®-lined cap and heated with stirring at 105° C. for 45 min. Additional N,N'-dimethylethylenediamine (10 µl, 0.1 mmol) was added, and the mixture was heated at 105° C. for 8 hr. The mixture was cooled, filtered (ethyl acetate rinse), and then the filtrate was evaporated. The residue was chromatographed on silica gel using 1:2 hexanes/ethyl acetate as eluent to afford compound 10-1 (55 mg) as an oil.

Using the appropriate heterocycle in place of the 3-(trifluoromethyl)pyrazole employed in Step 10B, the compounds in the following table were synthesized:

TABLE 3

| Cmpd | Het | MW | MS | $t_R$ |
|---|---|---|---|---|
| 10-1 | | 488.51 | 489.0 | 5.89 |
| 10-2 | | 487.60 | 488.1 | 4.74 |
| 10-3 | | 491.59 | 492.1 | 5.83 |
| 10-4 | | 444.54 | 445.1 | 5.3 |
| 10-5 | | 461.56 | 462.0 | 4.95 |

TABLE 3-continued

| Cmpd | Het | MW | MS | $t_R$ |
|---|---|---|---|---|
| 10-6 | | 461.56 | 462.0 | 4.72 |
| 10-7 | | 419.53 | 420.0 | 5.35 |

Example 11

SYNTHESIS OF 7-(1-METHOXY-PROPYL)-3-(2-METHOXY-4-PYRAZOL-1-YL-PHENYL)-1,5-DIMETHYL-1H-PYRAZOLO[4,3-b]PYRIDINE

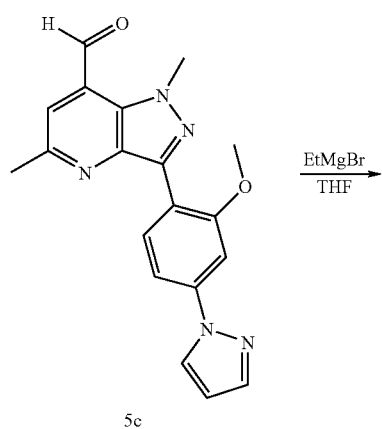

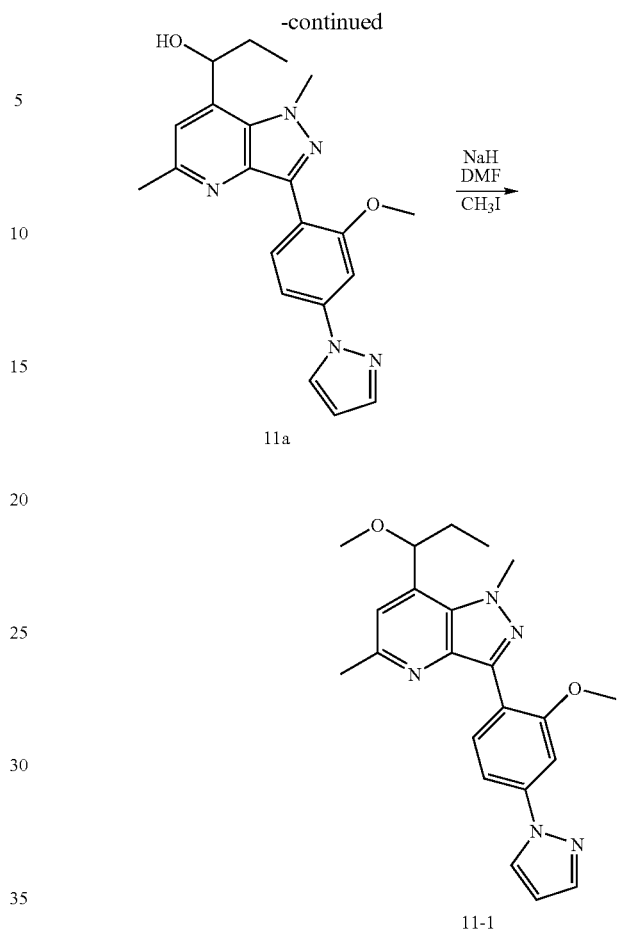

Step 11A:

Ethylmagnesium bromide (0.5 mL of a 3.0 M solution in ether, 1.5 mmol) was added to a solution of compound 5c (80 mg, 0.23 mmol) in THF (5 mL) at −78° C. After 5 min the reaction was quenched with aqueous ammonium chloride and the mixture was allowed to warm to RT. The mixture was extracted with ethyl acetate. The extracts were dried over sodium sulfate, and concentrated to afford an oil. This procedure was repeated with a 50 mg batch of compound 5c, and the combined resultant compounds were purified by silica gel chromatography eluting with 1:3 hexanes/ethyl acetate to afford compound 11a (23 mg) as a yellow solid.

Step 11B:

Sodium hydride (20 mg of a 60% dispersion in oil, 0.48 mmol) was added to a solution of compound 11a (22 mg, 0.058 mmol) in DMF (0.2 mL) at RT. After 5 min, methyl iodide (10 μl, 0.16 mmol) was added and the mixture was stirred for 10 min. Aqueous sodium dihydrogenphosphate (10%) was added and the mixture was extracted with DCM. The combined extracts were dried over sodium sulfate and concentrated to afford an oil which was purified by silica gel chromatography using 1:1 hexanes/ethyl acetate as eluent giving compound 11-1 (21 mg) as a yellow oil; MW=391.47; MS: [M+H]=392.0; $t_R$=4.88.

Example 12

SYNTHESIS OF 3-(2-METHOXY-4-PYRAZOL-1-YL-PHENYL)-1,5-DIMETHYL-7-[PHENYL-(2,2,2-TRIFLUORO-ETHOXY)-METHYL]-1H-PYRAZOLO[4,3-B]PYRIDINE

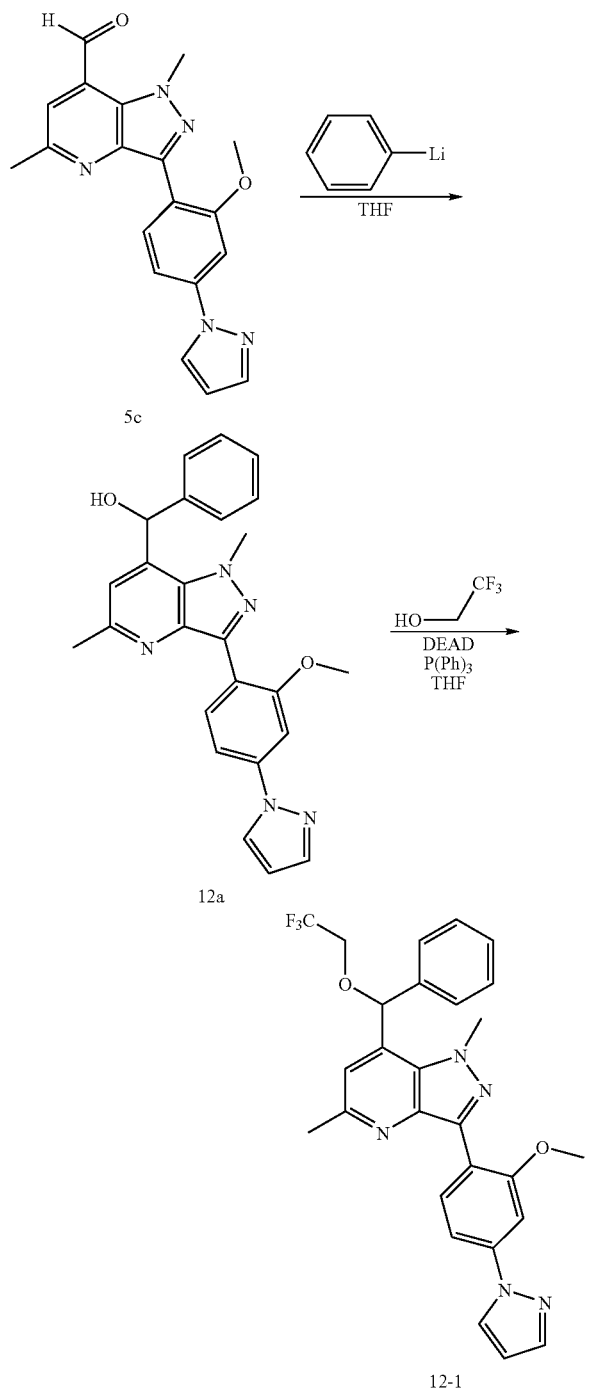

Step 12A:

Phenyllithium (0.25 mL of a 1.9 M solution in cyclohexane/ether, 0.48 mmol) was added to a solution of compound 5c (45 mg, 0.13 mmol) in THF (5 mL) at RT. Extractive workup followed by silica gel chromatography (1:3 hexanes/ethyl acetate) to afford compound 12a (36 mg) as a yellow oil.

Step 12B:

A solution of compound 12a (35 mg, 0.08 mmol) in anhydrous THF (0.4 mL) was treated successively with 2,2,2-trifluoroethanol (0.057 mL, 0.8 mmol), diethylazodicarboxylate (0.03 mL, 0.18 mmol), and triphenylphosphine (50 mg, 0.19 mmol). The mixture was stirred at RT for 8 hr then heated in a sealed vial at 69° C. for 15 hr. The solvent was evaporated and the residue purified by silica gel chromatography followed by ion exchange chromatography (Varian SCX cartridge, elution with 1:1 DCM/methanol followed by 1.0 M ammonia in methanol) followed by preparative thin-layer chromatography to afford compound 12-1 (5 mg) as a yellow oil; MW=507.514; $t_R$=7.27.

Example 13

SYNTHESIS OF [1,5-DIMETHYL-3-(2-METHYL-4-PYRAZOL-1-YL-PHENYL)-1H-PYRAZOLO[4,3-b]PYRIDIN-7-YL]-DIETHYL-AMINE

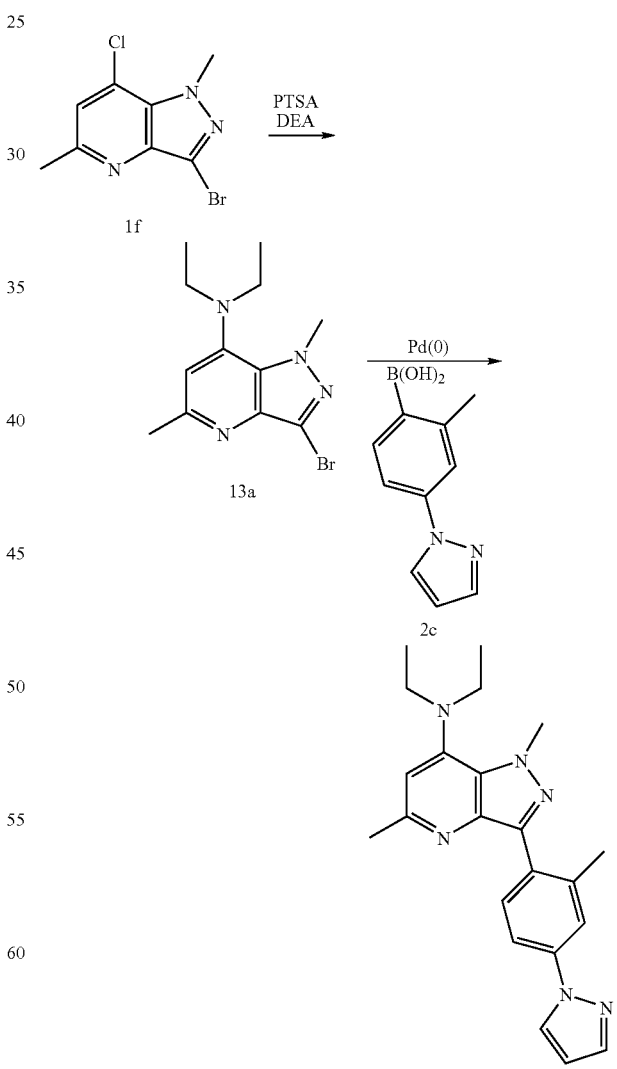

Step 13A:

A solution of compound 1f (50 mg, 0.19 mmol), pTSA-H$_2$O (50 mg, 0.26 mmol) and diethylamine (200 mg, 3.31 mmol) was heated at 180° C. in a sealed vial for 17 min in a microwave oven. The excess reagent was evaporated and ethyl acetate (5 mL) was added. The organic layer was washed with saturated aqueous sodium bicarbonate (5 mL) and brine (5 mL), dried over magnesium sulfate and purified by silica gel chromatography using 1:1 hexanes/ethyl acetate as eluent to afford (1,5-dimethyl-1H-pyrazolo[4,3-b]pyridin-7-yl)-diethyl-amine (compound 13a, 40 mg) as an oil.

Step 13B:

A mixture of compound 13a (40 mg, 0.13 mmol), compound 2c (41 mg, 0.20 mmol), tetrakis(triphenylphosphine)palladium(0) (15 mg, 0.013 mmol), aqueous sodium carbonate (0.3 mL of a 2 M solution, 0.6 mmol), toluene (2 mL), and ethanol (2 mL) was heated at 100° C. with stirring for 16 hr in a sealed vial. The mixture was cooled, filtered, and purified by preparative HPLC to afford [1,5-dimethyl-3-(2-methyl-4-pyrazol-1-yl-phenyl)-1H-pyrazolo[4,3-b]pyridin-7-yl]-diethyl-amine (compound 13-1, 3.5 mg).

Using the appropriate amine in place of the diethylamine employed in Step 13A, the compounds in the following table were synthesized:

TABLE 4

| Cmpd | R$_2$ | MW | MS | t$_R$ |
|---|---|---|---|---|
| 13-1 | (diethylamino) | 374.49 | 374.9 | 1.366 |
| 13-2 | (isopropylamino) | 360.46 | 361.1 | 4.537 |
| 13-3 | ((methoxymethyl)pyrrolidinyl) | 416.53 | 417.0 | 4.621 |

TABLE 4-continued

| Cmpd | R$_2$ | MW | MS | t$_R$ |
|---|---|---|---|---|
| 13-4 | (pyrrolidinyl) | 372.47 | 373.2 | 4.484 |

Example 14

SYNTHESIS OF [1,5-DIEMETHYL-3-(2-METHYL-4-PYRAZOL-1-YL-PHENYL)-1H-PYRAZOLO[4,3-B]PYRIDIN-7-YL]-BIS-(2-METHOXY-ETHYL)-AMINE

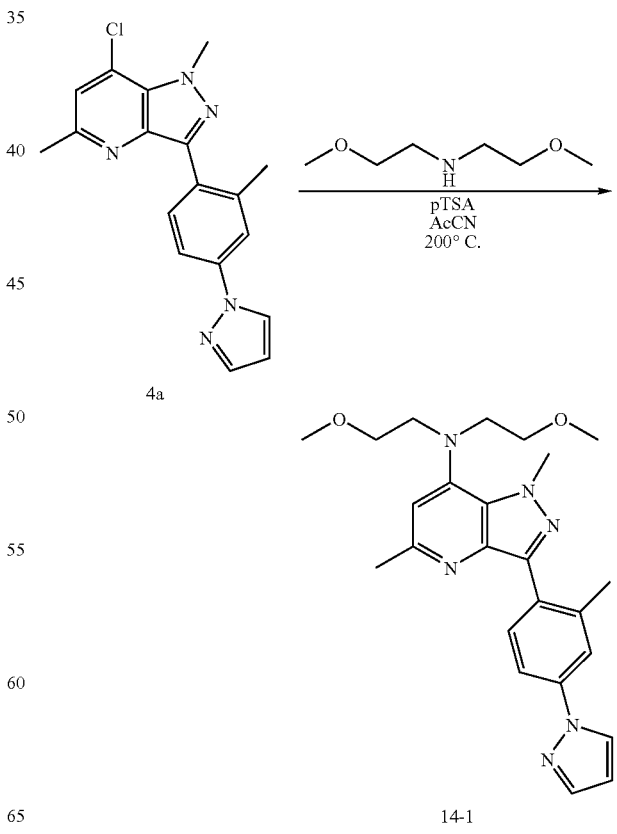

Step 14A:

To compound 4a (40 mg, 0.12 mmol) was added pTSA hydrate (41 mg, 0.24 mmol), bis(2-methoxyethyl)amine (0.032 mL, 0.24 mmol) and acetonitrile (0.5 mL). The reaction was heated to 200° C. in a microwave for 20 min. The reaction mixture was purified by HPLC/MS to afford [1,5-dimethyl-3-(2-methyl-4-pyrazol-1-yl-phenyl)-1H-pyrazolo[4,3-b]pyridin-7-yl]-bis-(2-methoxy-ethyl)-amine (compound 14-1, 11.2 mg) as a TFA salt.

Using the appropriate chloropyrazolopyridine and amine in place of those employed in Step 14A, the compounds in the following table were synthesized:

TABLE 5

| Cmpd | $R_2$ | $R_6$ | MW | MS | $t_R$ |
|---|---|---|---|---|---|
| 14-1 | methoxyethyl-N-methoxyethyl | $CH_3$ | 434.54 | 435.0 | 4.458 |
| 14-2 | (2-methoxymethyl)pyrrolidinyl | OMe | 432.53 | 433.2 | 4.73 |
| 14-3 | ethyl-N-methyl | $CH_3$ | 360.46 | 361.0 | 4.399 |
| 14-4 | 2-ethyl-5-methylimidazol-1-yl | $CH_3$ | 411.51 | 412.0 | 4.756 |
| 14-5 | 2-propylimidazol-1-yl | $CH_3$ | 411.51 | 412.0 | 4.923 |

TABLE 5-continued
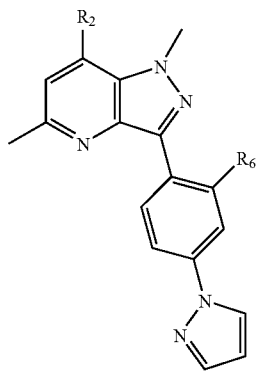
| Cmpd | R₂ | R₆ | MW | MS | $t_R$ |
|---|---|---|---|---|---|
| 14-6 | 2-ethyl-imidazol-1-yl | CH₃ | 397.48 | 398.0 | 4.72 |
| 14-7 | 7-azaindol-1-yl | CH₃ | 419.49 | 419.9 | 6.115 |
| 14-8 | 2-isopropyl-imidazol-1-yl | CH₃ | 411.51 | 412.0 | 4.857 |
| 14-9 | N-(2-methoxyethyl)-N-ethylamino | CH₃ | 404.52 | 405.1 | 4.81 |
| 14-10 | N-(2-methoxyethyl)-N-methylamino | CH₃ | 390.49 | 391.0 | 4.255 |

TABLE 5-continued

| Cmpd | R₂ | R₆ | MW | MS | $t_R$ |
|---|---|---|---|---|---|
| 14-11 | methoxyethyl(ethyl)amino-methyl | -C(CF₃)F₂ | 458.49 | 459.0 | 5.083 |
| 14-12 | 1-(2-ethyl-4-methylimidazolyl)ethyl | -C(CF₃)F₂ | 465.48 | 466.0 | 5.09 |
| 14-13 | N-benzyl-N-(ethoxycarbonylmethyl)aminomethyl | -OCH₃ | 510.60 | 511.1 | 5.888 |
| 14-14 | 1-(2-(thiazol-2-yl)pyrazol-1-yl)ethyl | -OCH₃ | 468.54 | 469.0 | 6.252 |

TABLE 5-continued
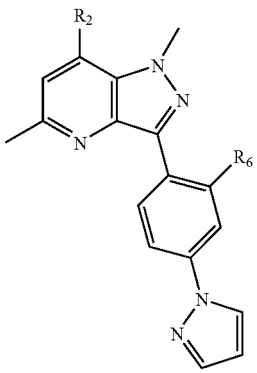
| Cmpd | R₂ | R₆ | MW | MS | $t_R$ |
|---|---|---|---|---|---|
| 14-15 | 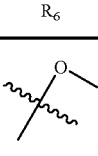 | 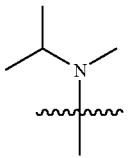 | 420.51 | 421.1 | 4.708 |
| 14-16 |  | 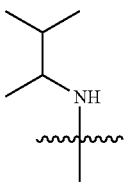 | 390.49 | 391.1 | 4.84 |
| 14-17 |  | 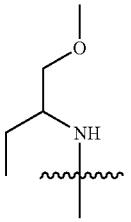 | 404.52 | 405.0 | 5.48 |
| 14-18 |  | | 420.51 | 421.0 | 5.009 |

Example 15

SYNTHESIS OF BENZYL-[3-(2-METHOXY-4-PYRAZOL-1-YL-PHENYL)-1,5-DIMETHYL-1H-PYRAZOLO[4,3-B]PYRIDIN-7-YL]-(3-METHYL-[1,2,4]OXADIAZOL-5-YLMETHYL)-AMINE

Example 16

SYNTHESIS OF BENZYL-[1,5-DIMETHYL-3-(2-METHYL-4-PYRAZOL-1-YL-PHENYL)-1H-PYRAZOLO[4,3-B]PYRIDIN-7-YL]-AMINE AND BENZYL-[1,5-DIMETHYL-3-(2-METHYL-4-PYRAZOL-1-YL-PHENYL)-1H-PYRAZOLO[4,3-B]PYRIDIN-7-YL]-PROPYL-AMINE

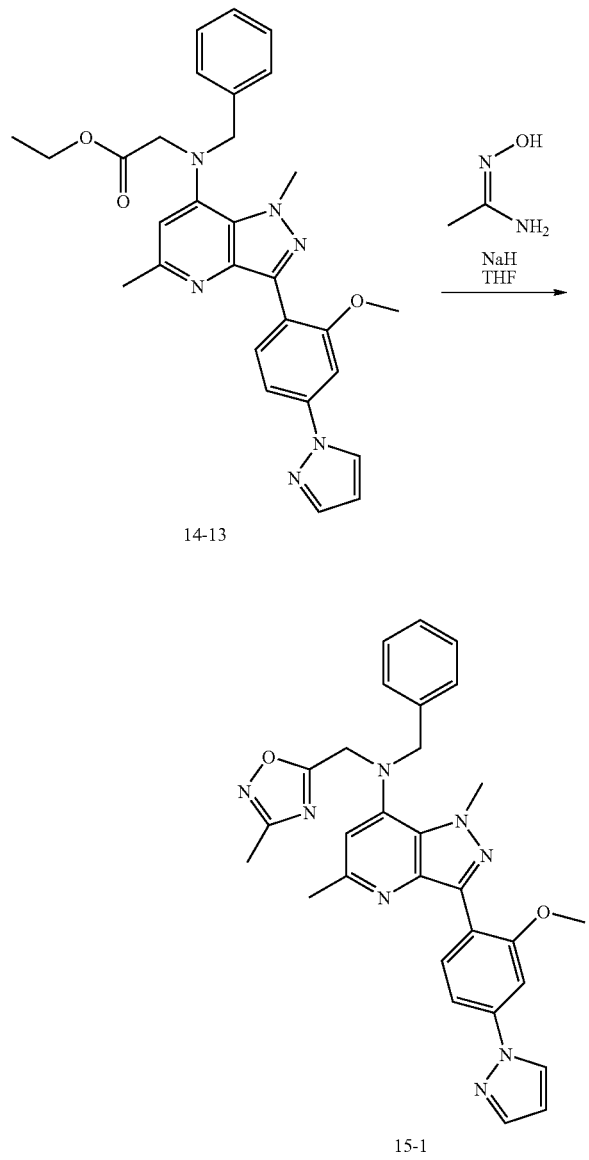

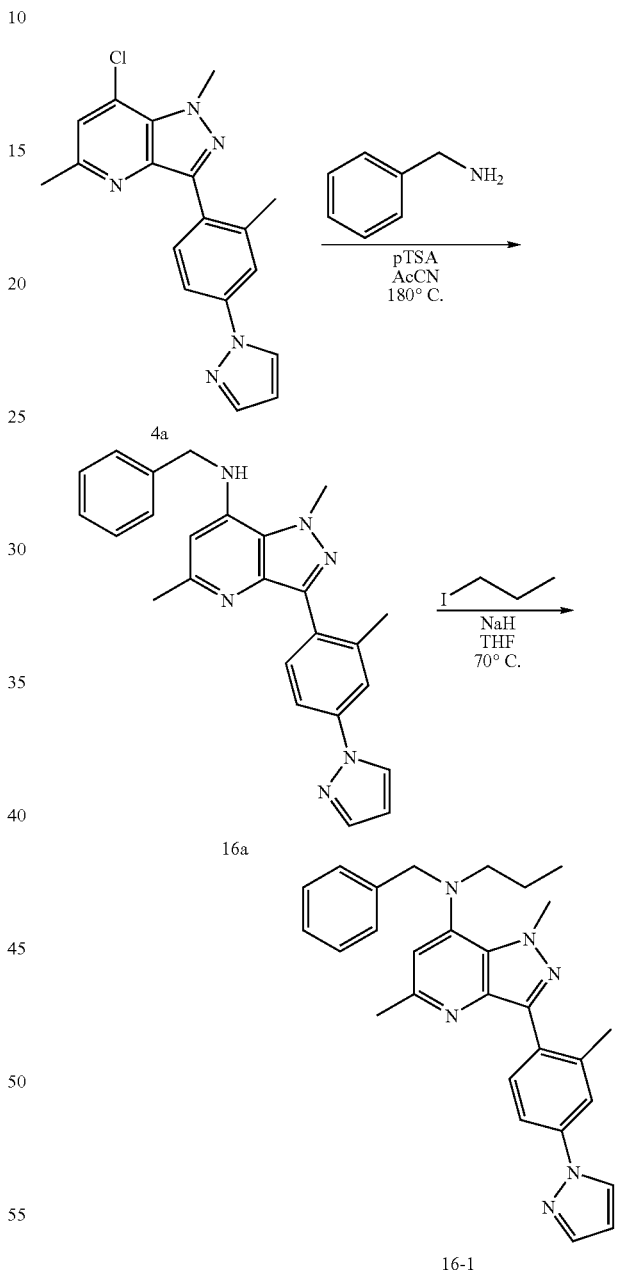

Step 15A:

Sodium hydride (3 mg, 60% suspension in mineral oil, 0.08 mmol) was added to a suspension of acetamidoxime (7 mg, 0.09 mmol) in THF (1 mL) under nitrogen at RT. The mixture was stirred for 10 min prior to introduction of compound 14-13 (32 mg, 0.06 mmol) in THF via syringe. The mixture was heated in a sealed tube at 90° C. for 2 hr. The cooled reaction mixture was diluted with methanol and purified with preparative reverse-phase HPLC to afford compound 15-1 as the TFA salt; MW=520.59; MS: [M+H]=521.1; $t_R$=5.385.

Step 16A:

To compound 4a (60 mg, 0.18 mmol) was added pTSA (62 mg, 0.36 mmol), benzylamine (0.040 mL, 0.36 mmol) and acetonitrile (0.5 mL). The reaction mixture was heated to 180° C. in a microwave for 15 min. Purification by preparative TLC using 10% MeOH/DCM as eluent afforded compound 16a (43 mg) as a yellow solid; LC/MS: [M+H]=409.2.

Step 16B:
To compound 16a (43 mg, 0.11 mmol) was added 1-iodopropane (0.053 mL, 0.33 mmol) and NaH (13 mg, 0.33 mmol, 60% in mineral oil) followed by anhydrous THF (0.5 mL). The reaction mixture was refluxed for 4 hours. Once cooled, the reaction was quenched with methanol and purified by HPLC/MS to afford compound 16-1 (20.8 mg) as a solid.

Using the appropriate chloropyrazolopyridine, amine and alkyl halide in place of those used in Steps 16A and 16B, the compounds in the following table were synthesized:

TABLE 6

| Cmpd | R$_2$ (NR$_{4a}$R$_{4b}$) | Amine (R$_{4a}$NH$_2$) | Alkyl halide (R$_{4b}$X) | R$_6$ | MW | MS | t$_R$ |
|---|---|---|---|---|---|---|---|
| 16-1 | benzyl(propyl)amine | benzylamine | I-propyl | CH$_3$ | 450.59 | 451.0 | 5.777 |
| 16-2 | (pyridin-2-ylmethyl)(propyl)amine | (pyridin-2-yl)methanamine | I-propyl | CH$_3$ | 451.58 | 452.0 | 4.823 |
| 16-3 | benzyl(propyl)amine | benzylamine | I-propyl | OCH$_3$ | 466.59 | 467.0 | 5.636 |
| 16-4 | bis(2-(pyridin-3-yl)ethyl)amine | 2-(pyridin-3-yl)ethanamine | I-propyl | CH$_3$ | 465.60 | 466.0 | 3.957 |
| 16-5 | ethyl(2-(pyridin-3-yl)ethyl)amine | 2-(pyridin-3-yl)ethanamine | I-propyl | CH$_3$ | 451.58 | 452.0 | 3.626 |
| 16-6 | ethyl(2,2,2-trifluoroethyl)amine | 2,2,2-trifluoroethanamine | I-ethyl | OCH$_3$ | 444.46 | 445.0 | 5.33 |

TABLE 6-continued

| Cmpd | R$_2$ (NR$_{4a}$R$_{4b}$) | Amine (R$_{4a}$NH$_2$) | Alkyl halide (R$_{4b}$X) | R$_6$ | MW | MS | t$_R$ |
|---|---|---|---|---|---|---|---|
| 16-7 | ethoxyethyl(ethyl)amino | H$_2$N-Et | Br-CH$_2$CH$_2$-OEt | CH$_3$ | 418.54 | 419.1 | 5.083 |
| 16-8 | (2-pyridylethyl)(isopropyl)amino | 2-(2-pyridyl)ethylamine | iPrBr | CH$_3$ | 465.60 | 466.0 | 3.943 |
| 16-9 | ethyl(isopropyl)amino | iPrNH$_2$ | EtI | OMe | 404.52 | 405.1 | 5.109 |
| 16-10 | methoxyethyl(isopropyl)amino | iPrNH$_2$ | Br-CH$_2$CH$_2$-OMe | OMe | 434.54 | 435.1 | 4.931 |
| 16-11 | (2,2,2-trifluoroethyl)(2-fluoroethyl)amino | CF$_3$CH$_2$NH$_2$ | Br-CH$_2$CH$_2$-F | OMe | 462.45 | 463.0 | 5.046 |

TABLE 6-continued

| Cmpd | R₂ (NR₄ₐR₄ᵦ) | Amine (R₄ₐNH₂) | Alkyl halide (R₄ᵦX) | R₆ | MW | MS | t_R |
|---|---|---|---|---|---|---|---|
| 16-12 | (cyclopropylmethyl)(cyclopropylmethyl)N– | cyclopropyl-CH₂-NH₂ | Br-CH₂-cyclopropyl | –OCH₃ | 442.56 | 443.1 | 5.679 |
| 16-13 | (cyclopropylmethyl)(isopropyl)N– | cyclopropyl-CH₂-NH₂ | I-iPr | –OCH₃ | 430.55 | 431.1 | 5.484 |
| 16-14 | (cyclopropylmethyl)(2-fluoroethyl)N– | cyclopropyl-CH₂-NH₂ | Br-CH₂CH₂-F | –OCH₃ | 434.52 | 435.1 | 4.949 |

Example 17

SYNTHESIS OF 7-(1-ETHYL-PROPOXY)-1,5-DIMETHYL-3-(2-METHYL-4-PYRAZOL-1-YL-PHENYL)-1H-PYRAZOLO[4,3-B]PYRIDINE

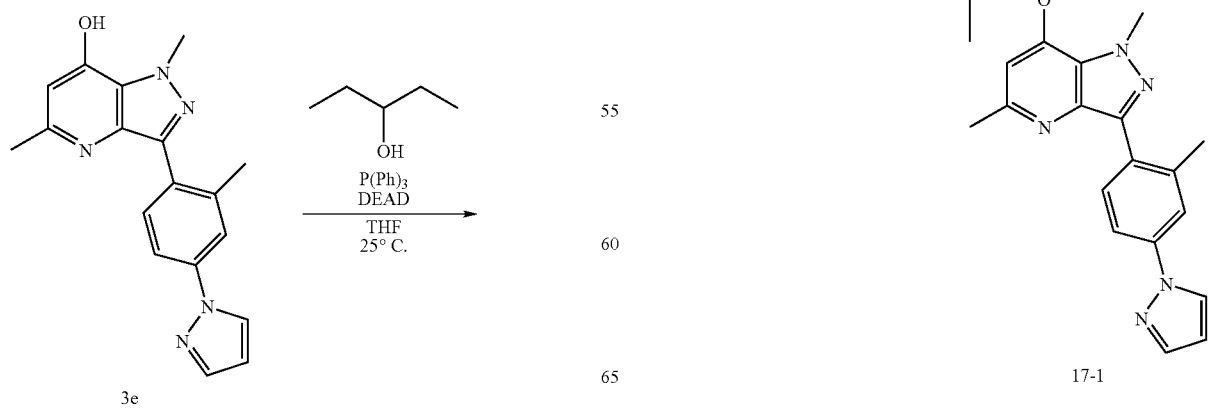

Step 17A:

To compound 3e (30 mg, 0.09 mmol) was added 3-pentanol (0.012 mL, 0.14 mmol), triphenylphosphine (0.14, 1.5 eq) and anhydrous THF (0.5 mL). A stream of nitrogen was blown into the reaction vessel after which it was capped and stirred at room temperature for 5 min. This was followed by the addition of diethyl azodicarboxylate (0.024 mL, 0.14 mmol). The reaction was stirred at room temperature overnight. The reaction mixture was diluted with methanol (0.5 mL) and purified by HPLC/MS to afford compound 17-1 (3.0 mg) as a TFA salt.

Using the appropriate hydroxypyrazolopyridine and alcohol in place of those employed in Step 17A, the compounds in the following table were synthesized:

TABLE 7

| Cmpd | R$_2$ | R$_6$ | MW | MS | t$_R$ |
|---|---|---|---|---|---|
| 17-1 | (3-pentyl ether) | CH$_3$ | 389.50 | 390.2 | 5.829 |
| 17-2 | (3-pentyl ether) | OCH$_3$ | 405.45 | 406.2 | 5.713 |
| 17-3 | (1,3-difluoro-2-propyl ether) | OCH$_3$ | 413.43 | 414.1 | 4.832 |
| 17-4 | (1,3-difluoro-2-propyl ether) | CH$_3$ | 397.43 | 398.2 | 5.047 |

TABLE 7-continued

| Cmpd | R$_2$ | R$_6$ | MW | MS | t$_R$ |
|---|---|---|---|---|---|
| 17-5 | (1,3-dimethoxy-2-propyl ether) | OCH$_3$ | 437.50 | 438.0 | 4.837 |
| 17-6 | (2-butyl ether) | OCH$_3$ | 391.47 | 392.0 | 5.098 |
| 17-7 | (3-methoxy-2-propyl ether) | CH$_3$ | 405.50 | 406.0 | 5.071 |
| 17-8 | ((S)-2-butyl ether) | CH$_3$ | 375.47 | 376.0 | 5.112 |
| 17-9 | ((R)-2-butyl ether) | CH$_3$ | 375.47 | 376.0 | 5.134 |

TABLE 7-continued
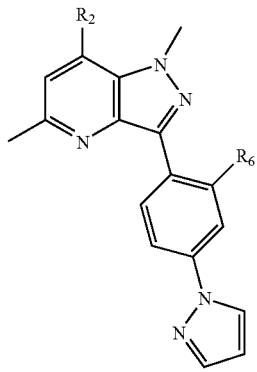
| Cmpd | R₂ | R₆ | MW | MS | $t_R$ |
|---|---|---|---|---|---|
| 17-10 | (methoxypropoxy group) | CH₃ | 391.47 | 392.1 | 4.618 |
| 17-11 | (dimethoxy group) | CH₃ | 421.50 | 422.0 | 4.734 |
| 17-12 | (sec-butoxy, S) | OCH₃ | 391.47 | 392.0 | 5.433 |
| 17-13 | (sec-butoxy, R) | OCH₃ | 391.47 | 392.1 | 5.442 |
| 17-14 | (methoxymethyl sec-butoxy) | CF₃ | 459.47 | 460.0 | 5.679 |
| 17-15 | (bis-methoxymethyl) | OCH₃ | 421.50 | 422.1 | 5.071 |
TABLE 7-continued
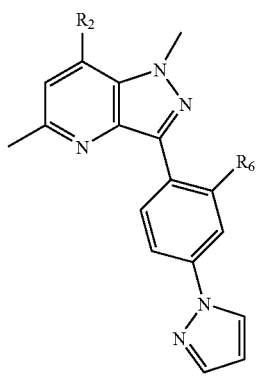
| Cmpd | R₂ | R₆ | MW | MS | $t_R$ |
|---|---|---|---|---|---|
| 17-16 | (methoxymethyl sec-butoxy) | Cl | 425.918 | 426.0 | 4.607 |
Example 18
SYNTHESIS OF 1-{3-METHOXY-4-[7-(1-METHOXYMETHYL-PROPOXY)-1,5-DIMETHYL-1H-PYRAZOLO[4,3-B]PYRIDIN-3-YL]-PHENYL}-1H-PYRROLE-2-CARBONITRILE
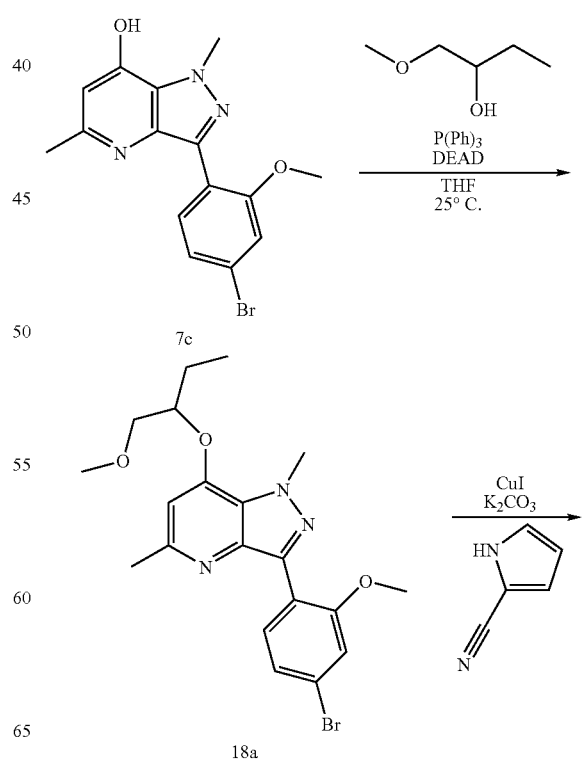

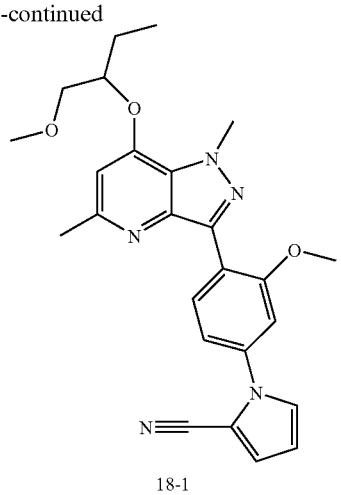

18-1

Step 18A:

Mitsunobu reaction of compound 7c with 1-methoxy-butan-2-ol, following the procedure of Example 17, afforded 3-(4-Bromo-2-methoxy-phenyl)-7-(1-methoxymethyl-propoxy)-1,5-dimethyl-1H-pyrazolo[4,3-b]pyridine (compound 18a).

Step 18B:

Copper(I) iodide catalyzed Buchwald reaction of compound 18a with 2-cyanopyrrole, following the procedure of Example 10, Step 10B, afforded 1-{3-Methoxy-4-[7-(1-methoxymethyl-propoxy)-1,5-dimethyl-1H-pyrazolo[4,3-b]pyridin-3-yl]-phenyl}-1H-pyrrole-2-carbonitrile (compound 18-1).

Using the appropriate heterocycle in place of the 2-cyanopyrrole employed in Step 18B, the compounds in the following table were synthesized:

TABLE 8

| Cmpd | Het | MW | MS | $t_R$ |
|---|---|---|---|---|
| 18-1 | (2-cyanopyrrol-1-yl) | 445.52 | 446.0 | 5.325 |

TABLE 8-continued

| Cmpd | Het | MW | MS | $t_R$ |
|---|---|---|---|---|
| 18-2 | (pyrrol-1-yl) | 420.51 | 421.0 | 5.024 |

Example 19

SYNTHESIS OF 2-[3-(2-METHOXY-4-PYRAZOL-1-YL-PHENYL)-1,5-DIMETHYL-1H-PYRAZOLO[4,3-B]PYRIDIN-7-YLOXY]-BUTYRIC ACID METHYL ESTER

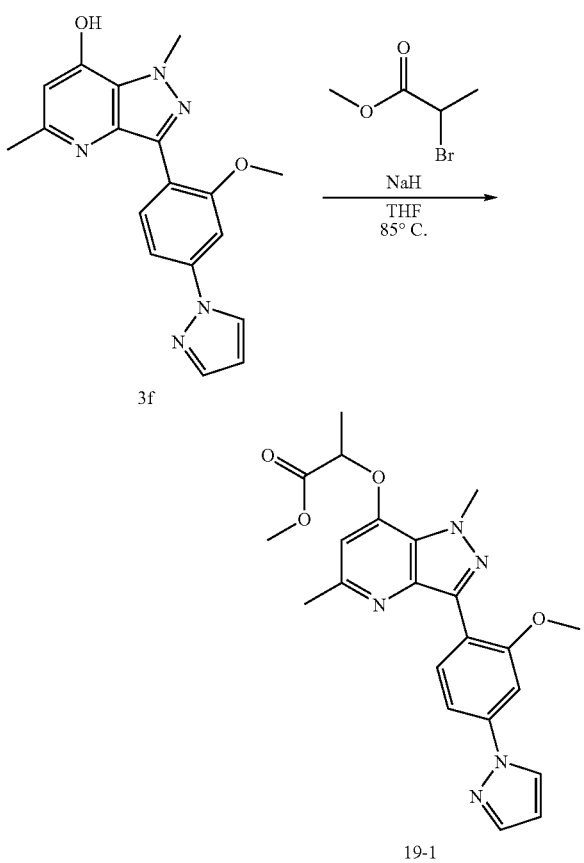

19-1

Step 19A:

To compound 3f (40 mg, 0.12 mmol) was added (+/−)-methyl-2-bromopropionate (34 mg, 0.18 mmol), NaH (10 mg, 0.24 mmol, 60% in mineral oil) and anhydrous THF (0.5 mL). After stirring for 5 min at RT, the reaction mixture was heated in a sealed tube at 85° C. for 12 hours. After cooling, the reaction was quenched with methanol (0.5 mL) and purified by HPLC/MS to afford compound 19-1 (11 mg) as a solid TFA salt.

Depending on the bromide employed in Step 19A, the compounds in the following table were synthesized. Compound 19-3 was synthesized from compound 19-2 using the protocol of Example 15:

TABLE 9

| Cmpd | R$_2$ | MW | MS | t$_R$ |
|---|---|---|---|---|
| 19-1 | | 421.46 | 422.0 | 4.874 |
| 19-2 | | 435.48 | 436.0 | 5.015 |
| 19-3 | | 459.51 | 460.1 | 4.845 |

Example 20

CRF Receptor Binding Activity

The compounds of this invention may be evaluated for binding activity to the CRF receptor by a standard radioligand binding assay as generally described by Grigoriadis et al. (*Mol. Pharmacol* vol 50, pp 679-686, 1996) and Hoare et al. (*Mol. Pharmacol* vol 63 pp 751-765, 2003). By utilizing radiolabeled CRF ligands, the assay may be used to evaluate the binding activity of the compounds of the present invention with any CRF receptor subtype.

Briefly, the binding assay involves the displacement of a radiolabeled CRF ligand from the CRF receptor. More specifically, the binding assay is performed in 96-well assay plates using 1-10 kg cell membranes from cells stably transfected with human CRF receptors. Each well receives about 0.05 mL assay buffer (e.g., Dulbecco's phosphate buffered saline, 10 mM magnesium chloride, 2 mM EGTA) containing compound of interest or a reference ligand (for example, sauvagine, urocortin I or CRF), 0.05 mL of [$^{125}$I] tyrosine-sauvagine (final concentration ~150 pM or approximately the K$_D$ as determined by Scatchard analysis) and 0.1 mL of a cell membrane suspension containing the CRF receptor. The mixture is incubated for 2 hours at 22° C. followed by separation of the bound and free radioligand by rapid filtration over glass fiber filters. Following three washes, the filters are dried and radioactivity (Auger electrons from $^{125}$I) is counted using a scintillation counter. All radioligand binding data may be analyzed using the non-linear least-squares curve-fitting programs Prism (GraphPad Software Inc) or XLfit (ID Business Solutions Ltd).

Example 21

CRF-Stimulated Adenylate Cyclase Activity

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (*Synapse* 1:572, 1987) with modifications to adapt the assay to whole cell preparations.

More specifically, the standard assay mixture may contain the following in a final volume of 0.1 mL: 2 mM L-glutamine, 20 mM HEPES, and 1 mM IMBX in DMEM buffer. In stimulation studies, whole cells with the transfected CRF receptors are plated in 96-well plates and incubated for 30 min at 37° C. with various concentrations of CRF-related and unrelated peptides in order to establish the pharmacological rank-order profile of the particular receptor subtype. Following the incubation, cAMP in the samples is measured using standard commercially available kits, such as cAMP-Screen™ from Applied Biosystems. For the functional assessment of the compounds, cells and a single concentration of CRF or related peptides causing 50% stimulation of cAMP production are incubated along with various concentrations of competing compounds for 30 min at 37° C., and cAMP determined as described above.

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A compound represented by the following structure:

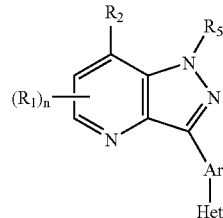

or a pharmaceutically acceptable salt, ester, or stereoisomer thereof,
wherein:
$R_1$ at each occurrence is independently $C_1$-$C_6$ alkyl;
n is 0, 1 or 2;
$R_2$ is $C_1$-$C_{10}$ alkyl, substituted $C_1$-$C_{10}$ alkyl, aryl, substituted aryl, arylalkyl, substituted arylalkyl, heterocyclyl, substituted heterocyclyl, —$OR_3$, or —$NR_{4a}R_{4b}$;
$R_3$ is $C_1$-$C_{10}$ alkyl, substituted $C_1$-$C_{10}$ alkyl, arylalkyl, substituted arylalkyl, $C_1$-$C_{10}$ alkoxyalkyl, substituted $C_1$-$C_{10}$ alkoxyalkyl, heterocyclealkyl, or substituted heterocyclealkyl;
$R_{4a}$ and $R_{4b}$ are the same or different and independently hydrogen, $C_1$-$C_{10}$ alkyl, substituted $C_1$-$C_{10}$ alkyl, arylalkyl, substituted arylalkyl, heteroarylalkyl, substituted heteroarylalkyl, $C_1$-$C_{10}$ alkoxyalkyl or substituted $C_1$-$C_{10}$ alkoxyalkyl, with the proviso that $R_{4a}$ and $R_{4b}$ cannot both be hydrogen;
$R_5$ is hydrogen or $C_1$-$C_6$ alkyl;
Ar is substituted phenyl, pyridyl or substituted pyridyl; and
Het is heterocyclyl or substituted heterocyclyl.

2. A compound according to claim 1, wherein $R_1$ is methyl.

3. A compound according to claim 1, wherein n is 1.

4. A compound according to claim 1, wherein $R_2$ is $C_1$-$C_6$ alkyl.

5. A compound according to claim 1, wherein $R_2$ is substituted aryl.

6. A compound according to claim 1, wherein $R_2$ is substituted heteroaryl.

7. A compound according to claim 1, wherein $R_2$ is —$OR_3$.

8. A compound according to claim 7, wherein $R_3$ is $C_1$-$C_6$ alkyl, substituted $C_1$-$C_6$ alkyl, $C_1$-$C_6$ alkoxyalkyl or heteroarylalkyl.

9. A compound according to claim 1, wherein $R_2$ is —$NR_{4a}R_{4b}$.

10. A compound according to claim 9, wherein $R_{4a}$ and $R_{4b}$ are independently $C_1$-$C_6$ alkyl.

11. A compound according to claim 1, wherein $R_5$ is methyl.

12. A compound according to claim 1, wherein Het is substituted heterocyclyl.

13. A compound according to claim 1, wherein each of $R_1$ and $R_5$ is methyl.

14. A compound according to claim 13, wherein n is 1.

15. A compound according to claim 14, wherein Ar-Het is

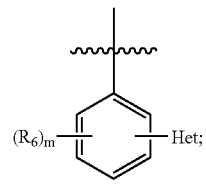

wherein:
m is 1, 2, 3 or 4; and
$R_6$ at each occurrence is independently $C_1$-$C_6$ alkyl, substituted $C_1$-$C_6$ alkyl, $C_1$-$C_6$ alkoxy or halogen.

16. A compound according to claim 15, wherein $R_6$ is selected from the group of methyl, methoxy and trihalomethyl.

17. A compound according to claim 16, wherein Het is pyridyl or substituted pyridyl.

18. A compound according to claim 17, wherein Het is pyridyl.

19. A pharmaceutical composition comprising a pharmaceutically acceptable carrier or diluent and a pharmaceutically effective amount of a compound represented by the following structure:

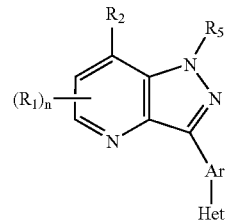

or a pharmaceutically acceptable salt, ester, or stereoisomer thereof,
wherein:
$R_1$ at each occurrence is independently $C_1$-$C_6$ alkyl;
n is 0, 1 or 2;
$R_2$ is $C_1$-$C_{10}$ alkyl, substituted $C_1$-$C_{10}$ alkyl, aryl, substituted aryl, arylalkyl, substituted arylalkyl, heterocyclyl, substituted heterocyclyl, —$OR_3$, or —$NR_{4a}R_{4b}$;
$R_3$ is $C_1$-$C_{10}$ alkyl, substituted $C_1$-$C_{10}$ alkyl, arylalkyl, substituted arylalkyl, $C_1$-$C_{10}$ alkoxyalkyl, substituted $C_1$-$C_{10}$ alkoxyalkyl, heterocyclealkyl, or substituted heterocyclealkyl;
$R_{4a}$ and $R_{4b}$ are the same or different and independently hydrogen, $C_1$-$C_{10}$ alkyl, substituted $C_1$-$C_{10}$ alkyl, arylalkyl, substituted arylalkyl, heteroarylalkyl, substituted heteroarylalkyl, $C_1$-$C_{10}$ alkoxyalkyl or substituted $C_1$-$C_{10}$ alkoxyalkyl, with the proviso that $R_{4a}$ and $R_{4b}$ cannot both be hydrogen;
$R_5$ is hydrogen or $C_1$-$C_6$ alkyl;
Ar is substituted phenyl, pyridyl or substituted pyridyl; and
Het is heterocyclyl or substituted heterocyclyl.

20. A composition according to claim 19, wherein $R_1$ is methyl.

21. A composition according to claim 19, wherein n is 1.

22. A composition according to claim 19, wherein $R_2$ is $C_1$-$C_6$ alkyl.

23. A composition according to claim 19, wherein $R_3$ is $C_1$-$C_6$ alkyl, substituted $C_1$-$C_6$ alkyl, $C_1$-$C_6$ alkoxyalkyl or heteroarylalkyl.

24. A composition according to claim 19, wherein $R_5$ is methyl.

25. A composition according to claim 19, wherein Het is substituted heterocycle.

26. A composition according to claim 19, wherein each of $R_1$ and $R_5$ is methyl.

27. A composition according to claim 26, wherein n is 1.

28. A composition according to claim 27, wherein Ar-Het is

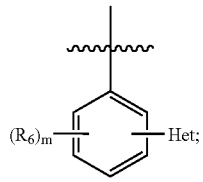

wherein:

m is 1, 2, 3 or 4; and $R_6$ at each occurrence is independently $C_1$-$C_6$ alkyl, substituted $C_1$-$C_6$ alkyl, $C_1$-$C_6$ alkoxy or halogen.

29. A composition according to claim 28, wherein $R_6$ is selected from the group of methyl, methoxy and trihalomethyl.

30. A composition according to claim 29, wherein Het is pyridyl or substituted pyridyl.

31. A composition according to claim 30, wherein Het is pyridyl.

32. A method for the treatment of a disease or condition selected from the group consisting of depression, anxiety, and irritable bowel syndrome, in a human comprising administering to said human a pharmaceutical composition comprising a pharmaceutically acceptable carrier or diluent and a pharmaceutically effective amount of a compound represented by the following structure

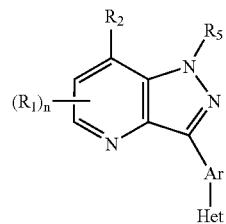

or a pharmaceutically acceptable salt, ester, or stereoisomer thereof wherein:

$R_1$ at each occurrence is independently $C_1$-$C_6$ alkyl;

n is 0, 1 or 2;

$R_2$ is $C_1$-$C_{10}$ alkyl, substituted $C_1$-$C_{10}$ alkyl, aryl, substituted aryl, arylalkyl, substituted arylalkyl, heterocyclyl, substituted heterocyclyl, —$OR_3$, or —$NR_{4a}R_{4b}$;

$R_3$ is $C_1$-$C_{10}$ alkyl, substituted $C_1$-$C_{10}$ alkyl, arylalkyl, substituted arylalkyl, $C_1$-$C_{10}$ alkoxyalkyl, substituted $C_1$-$C_{10}$ alkoxyalkyl, heterocyclealkyl, or substituted heterocyclealkyl;

$R_{4a}$ and $R_{4b}$ are the same or different and independently hydrogen, $C_1$-$C_{10}$ alkyl, substituted $C_1$-$C_{10}$ alkyl, arylalkyl, substituted arylalkyl, heteroarylalkyl, substituted heteroarylalkyl, $C_1$-$C_{10}$ alkoxyalkyl or substituted $C_1$-$C_{10}$ alkoxyalkyl, with the proviso that $R_{4a}$ and $R_{4b}$ cannot both be hydrogen;

$R_5$ is hydrogen or $C_1$-$C_6$ alkyl;

Ar is substituted phenyl, pyridyl or substituted pyridyl; and

Het is heterocyclyl or substituted heterocyclyl.

33. A method according to claim 32, wherein the disease or condition is depression.

34. A method according to claim 32, wherein the disease or condition is anxiety.

35. A method according to claim 32, wherein the disease or condition is irritable bowel syndrome.

* * * * *